(12) United States Patent
Byzova

(10) Patent No.: US 9,981,018 B2
(45) Date of Patent: May 29, 2018

(54) COMPOSITIONS AND METHODS FOR MODULATING TOLL-LIKE RECEPTOR 2 ACTIVATION

(71) Applicant: The Cleveland Clinic Foundation, Cleveland, OH (US)

(72) Inventor: Tatiana Byzova, Pepper Pike, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days. days.

(21) Appl. No.: 13/709,918

(22) Filed: Dec. 10, 2012

(65) Prior Publication Data

US 2013/0102536 A1 Apr. 25, 2013

Related U.S. Application Data

(63) Continuation of application No. PCT/US2011/039562, filed on Jun. 8, 2011.

(60) Provisional application No. 61/352,651, filed on Jun. 8, 2010.

(51) Int. Cl.
| | |
|---|---|
| *A61K 8/49* | (2006.01) |
| *A61Q 7/00* | (2006.01) |
| *A61K 38/38* | (2006.01) |
| *A61Q 19/00* | (2006.01) |
| *A61K 47/64* | (2017.01) |
| *A61K 38/00* | (2006.01) |

(52) U.S. Cl.
CPC .......... *A61K 38/385* (2013.01); *A61K 8/4913* (2013.01); *A61K 47/64* (2017.08); *A61Q 7/00* (2013.01); *A61Q 19/00* (2013.01); *A61K 38/00* (2013.01)

(58) Field of Classification Search
CPC ...... A61K 38/385; A61K 38/03; A61K 38/00; A61K 8/4913; A61K 47/48246; A61Q 19/00; A61Q 7/00
See application file for complete search history.

(56) References Cited

U.S. PATENT DOCUMENTS

2010/0048664 A1* 2/2010 Old .................. C07D 207/333
514/422

FOREIGN PATENT DOCUMENTS

| JP | 07138227 | * | 5/1995 | ......... C07D 207/323 |
| JP | 3439249 B | * | 8/2003 | |
| WO | WO 2008143928 A1 | * | 11/2008 | ............... A61K 8/00 |

OTHER PUBLICATIONS

Isambert et al. Abstract of Phase I study of OM-174, a lipid A analogue, with assessment of immunological response, in patients with refractory solid tumors, BMC Cancer Apr. 2, 2013;13:172.*
Ebrahem et al., Carboxyethylpyrrole oxidative protein modifications stimulate neovascularization: Implications for age-related macular degeneration, PNAS, Sep. 5, 2006, vol. 103, No. 36, pp. 13480-13484 and correction p. 17722 of Oct. 17, 2006, vol. 103, No. 42.*
Salomon et al., Discovery of Carboxytehylpyrroles (CEPs): Critical Insights into AMD, Autism, Cancer, and Wound Healing from Basic Research on the Chemistry of Oxidized Phospholipids, Chem Res. Toxicol., 2011, 24, 1803-1816.*
Gu et al., Carboxypyrrole Protein Adducts and Autoantibodies, Biomarkers for Age-related Macular Degeneration, J. Biol. Chem. vol. 278, No. 43, pp. 42027-42035.*
Gu et al., Oxidatively Truncated Docosahexaenoate Phospholipids: Total Synthesis, Generation, and Peptide Adduction Chemistry, JOC, 2003, 68, 3749-3761.*
Blair and Sperry, Natural Products Containing a Nitrogen-Nitrogen Bond, J. Nat Prods., 2013, 76, 794-812.*
Gu et al., Carboxyethylpyrrole Protein Adducts and Autoantibodies, Biomarkers for Age-related Macular Degeneration, Jl. of Biol. Chem., vol. 278, No. 43, Oct. 24, 2003, pp. 42027-42027.*
Hlavacek et al., Steric Effects on Multivalent Ligand-Receptor Binding: Exclusion of Ligand Sites by Bound Cell Surface Receptors, Biophysical Jl., vol. 76, Jun. 1999, pp. 3031-3043.*
Osaka et al., ASK1-dependent recruitment and activation of macrophages induce hair growth in skin wounds, Jl. Cell Biol., vol. 176, No. 7, Mar. 26, 2007, pp. 903-909.*
Yano et al., Control of hair growth and follicle size by VEGF-mediated angiogenesis, Journal of Clinical Investigation, Feb. 2001, vol. 107, No. 4, pp. 409-417.*
Heidenreich et al., Angiogenesis drives psoriasis pathogenesis, Int. J. Exp. Path. (2009), 90, 232-248.*
Globe et al., The impact of itch symptoms in psoriasis: results from physician interviews and patient focus groups, Health and Quality of Life Outcomes 2009, 7:62, 10 pp.*
Machine translation of JP 3439249 B, Mitsuo Murayama, issued Aug. 29, 2003.*
Kim et al. Receptor-Mediated Mechanism Controlling Tissue Levels of Bioactive Lipid Oxidation Products, Circ Res. Jul. 31, 2015; 117(4): 321-332.*
Shimizu et al., Increased Macrophage Migration Inhibitory Factor (MIF) in the Sera of Patients with Extensive Alopecia Areata, Jl. Invest. Derm. 118:3, 2002, 555-557.*
Bek-Thomsen et al., Proteome Analysis of Human Sebaceous Follicle Infundibula Extracted from Healthy and Acne-Affected Skin, PLOS ONE, 2009, vol. 9, issue 9, 1-9.*
Gu et al., Carboxyethylpyrrole Protein Adducts and Autoantibodies, Biomarkers for Age-related Macular Degeneration, Jl. Biol. Chem., 278:43 2003, 42027-42035.*
Xiaoxia Z. West, PhD. Thesis entitled the Mechanisms of Carboxyalkylpyrrole Induced Angiogenesis, Case Western Reserve University, May 2012 date.*
Selleri et al., Toll-like receptor agonists regulate b-defensin 2 release in hair follicle, British Journal of Dermatology 2007 156, pp. 1172-1177.*
Carrasco et al., Photoactivation of ROS production in situ transiently activates cell proliferation in mouse skin and in the hair follicle stem cell niche promoting hair growth and wound healing, J Invest Dermatol. Nov. 2015; 135(11): 2611-2622.*
Malinin et al., Oxidation as "The Stress of Life", Aging, Sep. 2011, vol. 3, No. 9, 906-910.*

* cited by examiner

*Primary Examiner* — Karlheinz R. Skowronek
*Assistant Examiner* — Joseph Fischer
(74) *Attorney, Agent, or Firm* — Tarolli, Sundheim, Covell & Tummino LLP

(57) ABSTRACT

A method of promoting hair growth of a subject includes administering to follicle cells of the subject a therapeutically effective amount of a TLR2 agonist that promotes TLR2 activation and hair growth of the subject.

12 Claims, 23 Drawing Sheets

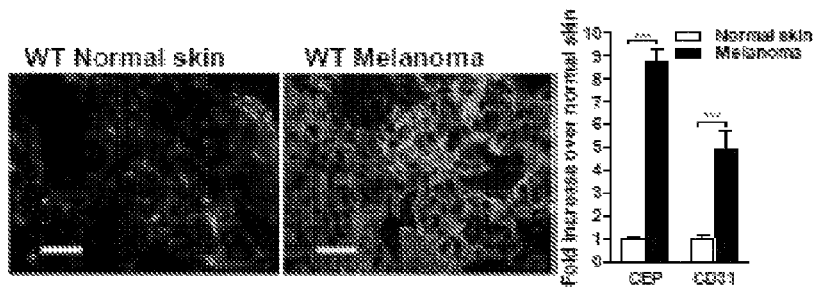
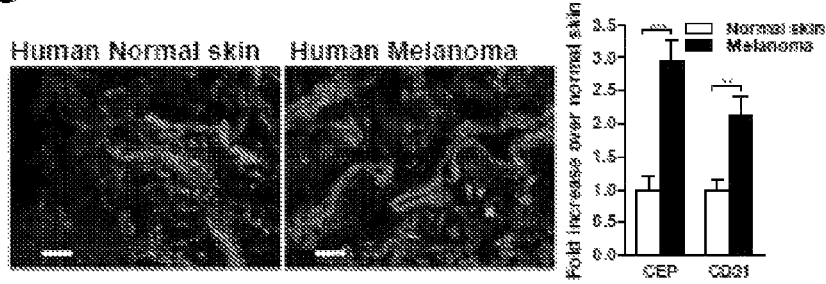
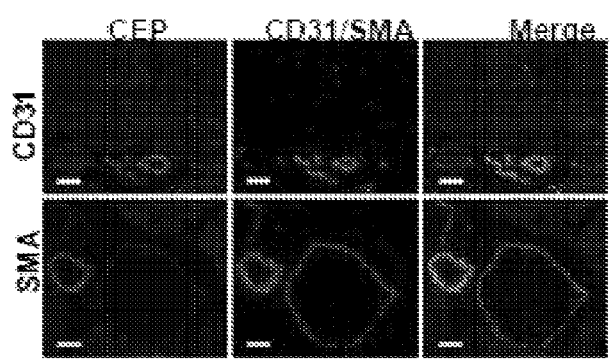
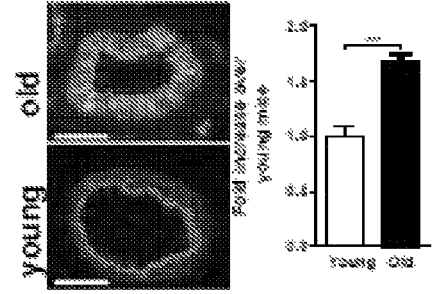
Fig. 1 c
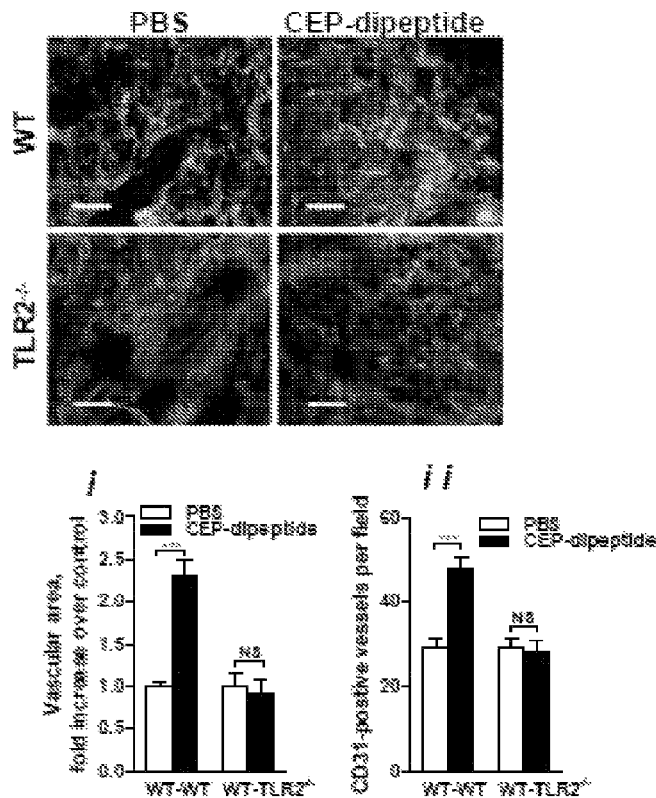
d
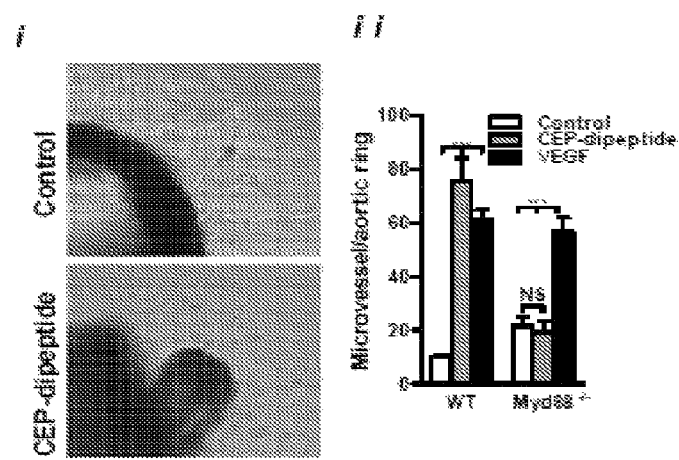
Fig. 4

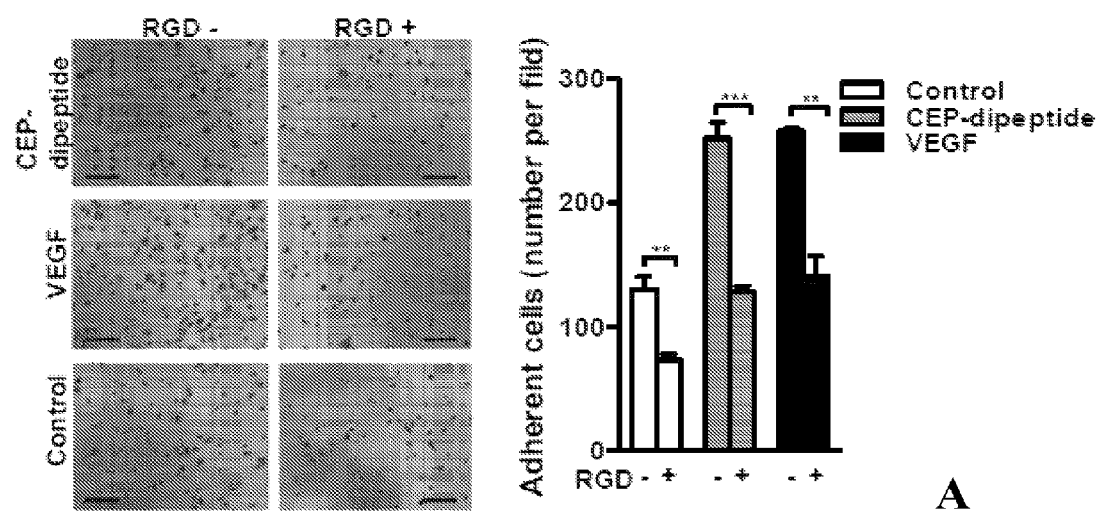
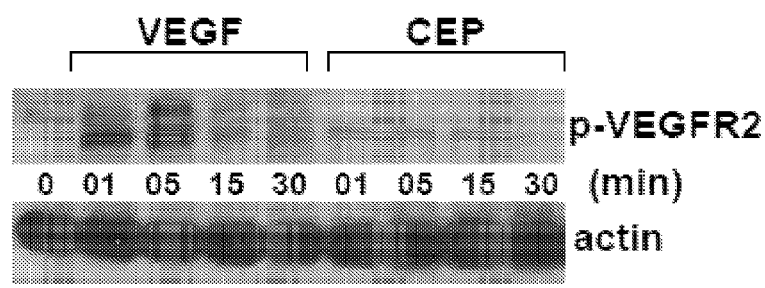
Fig. 6

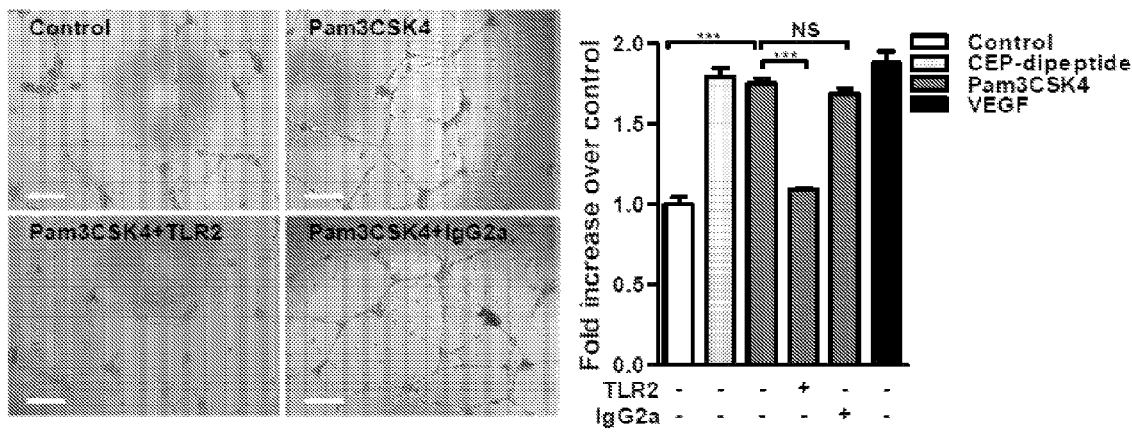
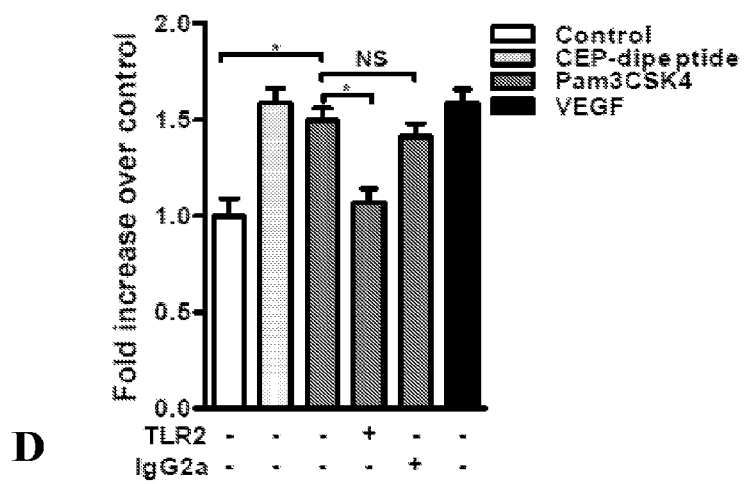
Fig. 7

Figs. 12A-B

COMPOSITIONS AND METHODS FOR MODULATING TOLL-LIKE RECEPTOR 2 ACTIVATION

RELATED APPLICATION

This application is a Continuation of PCT/US2011/039562, filed Jun. 8, 2011, which claims priority from U.S. Provisional Application No. 61/352,651, filed Jun. 8, 2010, the subject matter of which are incorporated herein by reference in their entirety.

GOVERNMENT FUNDING

This invention was made with government support under HL071625 awarded by The National Institutes of Health. The government has certain rights in the invention.

TECHNICAL FIELD

This application generally relates to compositions and methods for modulating toll-like receptor 2 (TLR2) activation, and more particularly to TLR2 agonists and antagonists for modulating TLR2 activation in endothelial and/or immune cells.

BACKGROUND OF THE INVENTION

The process of angiogenesis, or new blood vessel growth, may promote host defense and tissue repair or exacerbate disease conditions leading to organ dysfunction. In a number of pathologies, angiogenesis forms a strong reciprocal relationship with the process of inflammation. Recruited inflammatory cells facilitate neovascularization through the release of proangiogenic growth factors, including vascular endothelial growth factor. Newly formed blood vessels promote additional recruitment of inflammatory cells, thereby promoting the chronic aspect of inflammation. Various types of inflammatory cells, in particular of myeloid origin, are guided by and contribute to hyperoxidative conditions characterized by the presence of oxidized lipids and modified proteins.

Hyperoxidative conditions lead to the generation of a host of oxidative products, including hydroxy-ω-oxoalkenoic acids and their esters. When present in oxidized phospholipids, these molecules are recognized by scavenger receptor CD36 and contribute to atherosclerosis progression and platelet hyper-reactivity. Hydrolysis followed by reaction of the resulting unesterified hydroxy-ω-oxoalkenoic acids with proteins, or reaction of the esterified hydroxy-ω-oxoalkenoic acids with proteins followed by hydrolysis gives rise to a family of carboxyalkylpyrole protein adducts, among them 2-(ω-carboxyethyl)pyrrole adducts and similarly modified compounds. These adducts, which are present in oxidized LDL, can accumulate in atherosclerotic plaques. They are also found in the retina in photoreceptor outer segments and retinal pigmented endothelial cells, where they contribute to age-related macular degeneration progression, inter alia, by promoting choroidal neovascularization.

SUMMARY OF THE INVENTION

This application generally relates to compositions and methods for modulating toll-like receptor 2 (TLR2) activation, and more particularly to TLR2 agonists and antagonists for modulating TLR2 activation in cells expressing TLR2, such as endothelial cells and/or immune cells.

One aspect of the application relates to a method of modulating angiogenesis in a tissue of a subject. The method can include administering to tissue of the subject that includes endothelial cells a therapeutically effective amount of an agent that promotes or inhibits TLR2 activation.

Another aspect of the application relates to a topical or local formulation for treating a wound. The topical or local formulation can include a therapeutically effective amount of a TLR2 agonist that promotes TLR2 activation and at least one carrier. The topical formulation when administered to a wound of a subject can promote wound healing and/or accelerate wound closure.

A further aspect of the application relates to a pharmaceutical composition for treating a neoplastic disorder in a subject. The pharmaceutical composition can include an agent that inhibits complexing of TLR2 with carboxylalkyl pyrrole (CAP) adducts in endothelial cells, which are in or proximate neoplastic tissue of the subject.

Yet another aspect of the application relates to a method for promoting hair growth in a subject. The method can include administering to follicle cells of the subject a therapeutically effective amount of a TLR2 agonist that promotes TLR2 activation and hair growth of the subject.

Another aspect of the application relates to a topical formulation for promoting hair growth in a subject. The topical formulation can include a therapeutically effective amount of a TLR2 agonist that promotes TLR2 activation and at least one carrier. The topical formulation when administered to follicle cells of the subject can promote hair growth.

A further aspect of the application relates to a method of modulating in a subject one or more inflammatory and/or autoimmune diseases or disorders mediated by TLR2. The method can include administering to the subject a composition comprising an agent that modulates one or more CAP adducts in the subject.

BRIEF DESCRIPTION OF THE DRAWINGS

The foregoing and other features of the present invention will become apparent to those skilled in the art to which the present invention relates upon reading the following description with reference to the accompanying drawings, in which:

In FIG. 1A, co-staining for CEP and CD31 in normal skin (control) and wounded tissue collected 5 (5d) and 28 days (28d) after injury is shown (scale bar is 10 μm). Quantification of CEP staining is on the right. Bars represent fold increase over control (skin prior to injury) ±s.e.m., n=4. In FIG. 1B, CEP is present in bone marrow derived cells. Wound tissue was collected 5 days after injury from mice transplanted with bone marrow from DsRed expressing mice (scale bar is 10 μm). FIG. 1C shows co-staining for Gr-1, F4/80 and endogenous CEP in wound tissue before injury (0), 5 and 28 days after injury is indicated (scale bar is 10 μm). FIG. 1D shows that CEP is accumulated in highly vascularized tissues. Co-staining for CEP and CD31 in implanted mouse B16 melanoma and normal skin of C57B1/6 mice (WT) is shown (scale bar is 10 μm). Quantifications of CEP staining intensity and vascularization based on CD31 staining are shown on the right. Bars represent fold increase over control (normal skin) ±s.e.m., n=5. FIG. 1E shows that CEP and CD31 staining of human melanoma and normal skin are from the same subjects (scale bar is 10 μm). Quantifications of CEP staining intensity and vascularization (CD31) are shown on the right. Bars represent fold increase over control (normal skin) ±s.e.m., n=5. FIG. 1F shows that endogenous CEP in normal skeletal muscle tissue is present within the vessel wall. Co-staining for CEP and CD31-top; CEP and SMA-bottom (scale bar is 10 μm). FIG. 1G shows that CEP is accumulated in aging tissues. Tissue from 5 weeks (young), and 11 months (old) C57B1/6 mice were immunostained with anti-CEP and anti-CD31 antibodies (scale bar is 10 μm). Quantifications of CEP staining intensity is shown on the right. Bars represent fold increase over control (tissue from young mice) ±s.e.m., n=4;

FIG. 2A shows a HUVEC tube formation assay: left-representative micrographs of control (no treatment) and CEP-mouse serum albumin (MSA), CEP-dipeptide and 2-(ω-carboxypropyl)pyrrole (CPP)-human serum albumin (HAS) treated cells (scale bar is 60 μm); right—quantification of tube formation assay in the presence of CEP-MSA, CEP-dipeptide, CPP-HSA or VEGF (positive control) as indicated. Bars represent fold increase over control ±s.e.m., n=4. FIG. 2B shows a Mouse Lung Microvascular EC (MLEC) tube formation assay: left—representative micrographs of control (no treatments) and CEP-MSA, CEP-dipeptide and CPP-HSA treated cells (scale bar is 60 μm); right—quantification of tube formation assay (VEGF as positive control) as indicated. Bars represent fold increase over control ±s.e.m., n=4. FIG. 2C shows a Mouse aortic ring assay: left—representative micrographs of control (no treatments) and CEP-MSA, CEP-dipeptide and CPP-HSA treated cells; right—numbers of microvessels per aortic ring ±s.e.m. are shown at different time points after addition of CEP-MSA, CEP-dipeptide, CPP-HSA or VEGF (positive control) as indicated, n=5. FIG. 2D shows a HUVEC migration assay: cells were treated with CEP-MSA, CEP-dipeptide, CPP-HSA or VEGF at the indicated concentration or remained untreated (control). Bars represent percent increase over control ±s.e.m., n=4. FIGS. 2E-H show aortic ring (FIG. 2E and FIG. 2G) and tube formation (FIGS. 2F and 2H) assays using $CD36^{-/-}$ (FIGS. 2E and 2F) and $SR-B1^{-/-}$ (FIGS. 2G and 2H) mice; left-representative micrographs of control (no treatments) and CEP-MSA, CEP-dipeptide, CPP-HSA treated cells (scale bar is 60 μm); right—quantification of sprouts stimulated by CEP-MSA, CEP-dipeptide, CPP-HSA or VEGF (positive control) was performed as described in the Example below (bars represent fold increase over control ±s.e.m., n=5);

In FIG. 3A, HUVEC were stimulated with CEP or remained unstimulated. Tube formation assay was performed in the presence of blocking antibodies to TLR2 and TLR4 or non-immune isotype matched to IgG as indicated. Bars represent percent change over control ±s.e.m., n=4. FIG. 3B shows that oxidized adducts fail to induce angiogenesis in MLEC tube formation assay using $TLR2^{-/-}$ mice. Left-representative micrographs of control (no treatments), CEP-MSA, CEP-dipeptide and CPP-HSA treated cells, scale bar is 60 μm; right—bars represent fold increase in vascularization over control after stimulation with CEP-MSA, CEP-dipeptide, CPP-HSA or VEGF (positive control) as indicated, ±s.e.m., n=4. FIG. 3C shows that $TLR2^{+/+}$ but not $TLR2^{-/-}$ cells respond to stimulation with CEP-dipeptide in aortic ring assay. Left—representative micrographs of control (no treatments), CEP-dipeptide and VEGF treated aortic rings from $TLR2^{-/-}$ mice, scale bar is 60 μm; right—bars represent numbers of microvessels per ring ±s.e.m. after stimulation of $TLR2^{+/+}$ and $TLR2^{-/-}$ cells with CEP-dipeptide or VEGF as indicated, n=4. FIG. 3D shows that TLR2 ligand Pam3CSK4 induces angiogenesis in $TLR2^{+/+}$ but not $TLR2^{-/-}$ cells. Assay and quantifications are performed as in FIGS. 3C, 3E and 3F. CEP promotes angiogenesis in hind limb ischemia model using $TLR2^{+/+}$ but not $TLR2^{-/-}$ mice. Surgery, CEP injections, and tissue collection were performed as described in the Example below. In FIG. 3E, immunostaining for SMA is shown in PBS and CEP-treated tissues; scale bar is 40 μm. Bars represent vascular density and vascular area ±s.e.m. after treatment with CEP or PBS (control) as indicated, n=6. FIG. 3F shows LDI images of hind limb blood flow after treatment with CEP or PBS (control) as indicated are shown before, immediately after and 5 days post-hind limb ischemia (HLI) surgery. The perfusion ratio calculated as described in the Example below ±s.e.m. are shown, n=8 (days after surgery are indicated);

FIG. 4A shows that CEP promotes wound healing and vascularization in $TLR2^{+/+}$ but not $TLR2^{-/-}$ mice. Images of skin inner flap at 7 days after injury are shown. FIGS. 4B-C show that the response to CEP does not depend on TLR2 in bone-marrow derived cells. $TLR2^{-/-}$ and $TLR2^{+/+}$ mice were transplanted with $TLR2^{+/+}$ bone marrow as indicated and a wound assay was performed as in the Example below. FIG. 4B shows representative images of wounds are shown; scale bar is 1 mm Right—bars represent reductions in wound area ±s.e.m. upon treatment with CEP or PBS, n=5. FIG. 4C shows representative images of tissues stained for CD31 and CEP. Bottom: (i) bars represent fold changes in vascular area over control (PBS-treated) ±s.e.m. upon treatment with CEP-dipeptide, n=5; and (ii) fold changes in vascular density over control (PBS-treated) ±s.e.m. upon treatment with CEP dipeptide, n=5. FIG. 4D shows that CEP does not induce angiogenic response in $Myd88^{-/-}$ mice. Aortic ring assay was performed using $MyD88^{+/+}$ and $MyD88^{-/-}$ mice in the presence of CEP or VEGF as indicated; (i) representative micrographs; and (ii) bars represent numbers of microvessels per ring) ±s.e.m., n=5. FIG. 4E shows that CEP treatment promotes Rac1 activation in WT but not in $TLR2^{-/-}$ and $MyD88^{-/-}$ cells: (i) levels of Rac1GTP and total Rac1 in lysates of EC treated with or without CEP are shown; and (ii) bars represent fold increase in Rac1GTP calculated by densitometry analysis;

FIGS. 6A-B show that the CEP effect is integrin-dependent and VEGFR2-independent. For the cell adhesion assay, staining was done with hematoxylin (scale bar 40 μm, right—average cell number calculated in six independent fields ±s.e.m., RGD—integrin ligand competitor) (P<0.01, *P<0.001). In FIG. 6B, HUVEC cells were treated with VEGF or CEP-dipeptide for indicated period of time, lysed, and probed for phosphor-VEGFR2 (top) or total actin (bottom);

In FIG. 7A, HUVEC migration in the presence of TLR2 or TLR4 blocking antibodies is indicated (bars represent average cell number in six fields ±s.e.m.) (NS—not significant, ***P<0.001). In FIG. 7B, cell migration as % to control sample ±s.e.m. is shown (*P<0.05, *P<0.001). In FIG. 7C, CEP and VEGF-induced responses are shown for comparison (scale bar 60 μm; right—calculated average tube length ±s.e.m., n=4) (NS—not significant, *P<0.001). In FIG. 7D, the effects of CEP and VEGF are shown for comparison (fold increase over control ±s.e.m., n=4) (NS—not significant, *P<0.05);

FIG. 10A is a series of immunohistochemistry images showing vasculature in excised tumors from WT mice with WQT bone marrow, TLR2$^{-/-}$ mice with WT bone marrow (middle), and WT mice with TLR2$^{-/-}$ bone marrow (CD31 staining as an endothelial marker is shown in red) (NS—not significant);

DETAILED DESCRIPTION

Figure 1:
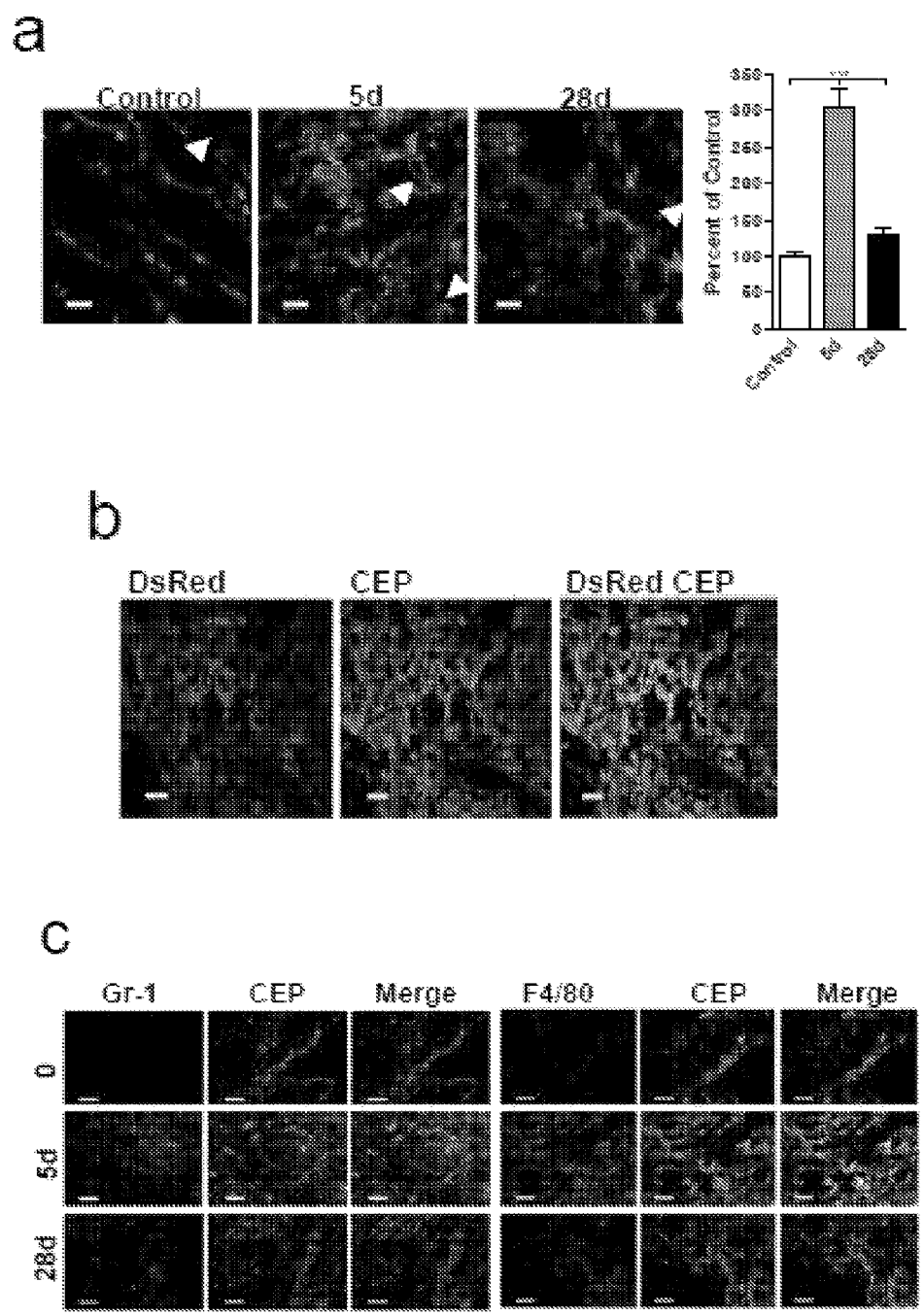
FIGS. 1A-G are series of immunostains showing that products of lipid oxidation represented by 2-(ω-carboxyethyl)pyrolle (CEP) are accumulated in wounded areas and present at high levels in tumors and in aging tissues.

All scientific and technical terms used in this application have meanings commonly used in the art unless otherwise specified. The definitions provided herein are to facilitate understanding of certain terms used frequently herein and are not meant to limit the scope of the application.

As used herein, the term "neoplastic disorder" can refer to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" can refer to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell" or "tumor cell".

Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

As used herein, the term "tumor" can refer to an abnormal mass or population of cells that result from excessive cell division, whether malignant or benign, and all pre-cancerous and cancerous cells and tissues.

As used herein, the terms "treating" or "treatment" of a disease or disorder can refer not only to ameliorating symptoms associated with the disease or disorder, but also preventing or delaying the onset of the disease or disorder, and/or lessening the severity or frequency of symptoms of the disease or disorder. Thus, the terms "treating" or "treatment" can include complete or incomplete eradication of the disease or disorder.

As used herein, the term "polymer" can refer to a molecule formed by the chemical union of two or more chemical units. The chemical units may be linked together by covalent linkages. The two or more combining units in a polymer can be all the same, in which case the polymer may be referred to as a homopolymer. The chemical units can also be different and, thus, a polymer may be a combination of the different units. Such polymers may be referred to as copolymers.

As used herein, the term "subject" can refer to any animal, including, but not limited to, humans and non-human animals (e.g., rodents, arthropods, insects, fish), non-human primates, ovines, bovines, ruminants, lagomorphs, porcines, caprines, equines, canines, felines, ayes, etc.), which is to be the recipient of a particular diagnostic and/or therapeutic application.

As used herein, the term "agonist" can refer to a substance that binds to a receptor of a cell and induces a response. An agonist often mimics the action of a naturally occurring substance, such as a ligand.

As used herein, the term "antagonist" can refer to a substance that attenuates the effects of an agonist.

As used herein, the terms "co-administration" or "co-administered" can refer to the administration of at least two different substances sufficiently close in time to modulate a physiological response (e.g., an immune response). Co-administration can refer to simultaneous administration, as well as temporally spaced order of up to several days apart and of at least two different substances in any order, either in a single dose or separate doses.

As used herein, the term "polypeptide" can refer to a molecule composed of monomers (amino acids) linearly linked by amide bonds (also known as peptide bonds). The term can indicate a molecular chain of amino acids and does not refer to a specific length of the product. Thus, peptides, dipeptides, tripeptides, oligopeptides, and proteins can be included within the definition of polypeptide. This term can also refer to the products of post-expression modifications of a polypeptide, such as glycosylation, hyperglycosylation, acetylation, phosphorylation, and the like. A polypeptide may be derived from a natural biological source or produced by recombinant technology, and is not necessarily translated from a designated nucleic acid sequence. A polypeptide may be generated by any manner known in the art, such as chemical synthesis.

As used herein, the terms "therapeutically effective amount" or "pharmaceutically effective amount" can refer to an amount of a substance and/or composition sufficient to affect a desired biological effect, such as a beneficial result, including, without limitation, prevention, diminution, amelioration or elimination of signs or symptoms of a disease or disorder. The total amount of each active component of a pharmaceutical composition or method may be sufficient to show a meaningful subject benefit (e.g., promoting wound healing). A "pharmaceutically effective amount" will depend upon the context in which it is being administered. A pharmaceutically effective amount may be administered in one or more prophylactic or therapeutic administrations. When applied to an individual active ingredient, administered alone, the terms can refer to that ingredient alone. When applied to a combination, the terms can refer to combined amounts of the active ingredients that result in the therapeutic effect, whether administered in combination, serially or simultaneously.

As used herein, the term "modulate" can refer to a change in the biological activity of a biologically active molecule, such as a cell receptor. Modulation can be an increase or a decrease in activity, a change in binding characteristics, or any other change in the biological, functional, or immunological properties of biologically active molecules.

This application relates to compositions and methods for modulating toll-like receptor 2 (TLR2) activation, and more particularly to TLR2 agonists and antagonists for modulating TLR2 activation in cells expressing TLR2, such as endothelial and/or immune cells. Although it is not necessary to understand the mechanisms in order to practice the methods or compositions described herein, and it is not intended that the application be so limited, it is shown herein that certain end products of lipid oxidation, such as ω-(2-carboxyalkyl)pyrrole (CAP) adducts and similar compounds are generated during inflammation and wound healing and accumulate at high levels in aging tissues and highly vascularized tumors. Carboxyalkyl pyrrole (CAP) adducts are recognized by TLR2 (but not TLR4) and lead to a VEGF-independent angiogenic response. Lipid oxidation products (e.g., CAP adducts) were found to promote angiogenic responses of endothelial cells by activating the TLR2 signaling pathway in a MyD88-dependent manner, leading to Rac1 activation which, in turn, facilitates integrin function.

CAP adducts if provided exogenously, as shown in the Examples, can treat hind limb ischemia, wound, and hair loss through TLR2 in a Myd88-dependent manner. Moreover, TLR2 antagonists if provided exogenously can substantially inhibit aberrant angiogenesis associated CAP adduct activation. This application therefore provides compositions and methods for modulating TLR2 activation in endothelial and/or immune cells to treat a variety of conditions, such as ischemia, wounds, dermatological disorders, cancer, autoimmune diseases, and inflammatory diseases.

One aspect of the application can include a method for modulating angiogenesis in a tissue of subject by administering to the tissue of the subject that includes at least one endothelial cell a therapeutically effective amount of an agent that promotes or inhibits TLR2 activation. Angiogenesis is a physiological process involving the growth of new blood vessels from pre-existing vessels.

In an aspect of the application, an agent that promotes angiogenesis in the tissue can include a TLR2 agonist. Generally, TLR2 agonists can include any substance or molecule that binds to or activates TLR2 present on cells (e.g., endothelial, endothelial precursor cells, and/or immune cells) and induces a response in the cells. For example, TLR2 agonists that bind to TLR2 can promote TLR2:Myd88 complex formation, lead to or increase binding of Rac1 with GTP, and/or promote integrin expression. Moreover, TLR2 agonists that bind to TLR2 can include any substance or molecule that binds to TLR2 and promotes migration of endothelial cells and/or endothelial precursor cells from a parent vessel wall into the surrounding matrix to a site of angiogenesis. By binding to or activating TLR2 in an endothelial cell, endothelial precursor cell, and/or immune cell, the TLR2 agonist can increase or promote angiogenesis in a subject.

One example of a TLR2 agonist can include a pyrrole adduct that preferentially binds TLR2 but not TLR4. In some embodiments, the pyrrole adduct can include CAP adducts, such as 2-(ω-carboxyheptyl)pyrrole (CHP), 2-(ω-carboxypropyl)pyrrole (CPP), and 2-(ω-carboxyethyl)pyrrole (CEP) adducts, as well as other pyrrole adducts that are generated from oxidation of poly-unsaturated fatty acids (PUFAs). For example, oxidative fragmentation of linoleic acid or 5-hydroxy-8-oxooct-6-enoic acid (HOOA) can produce 9-hydroxy-12-oxododec-10-enoic acid (HODA), respectively, which reacts with protein to generate CHP or CPP adducts, respectively. CHP and CPP protein adducts can arise not only from linoleic or arachidonic acid, but also from oxidation of other common PUFAs. For example, CEP protein adducts are a unique protein modification, which are derived from the oxidation of docosahexaenoate (DHA)-containing lipids.

In other embodiments of the application, pyrrole adducts can have the general formula X-A, wherein A is a substituted pyrrole and X is a peptide, dipeptide, polypeptide, small molecule, or polymer that includes an amine group that binds to the amine of the substituted pyrrole, or pharmaceutically acceptable salts thereof. For example, the substituted pyrrole adduct can have the following general formula:

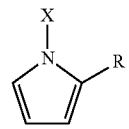

wherein X is a peptide, dipeptide, polypeptide, small molecule, or polymer that includes an amine group that binds to the amine of the substituted pyrrole, and R is a hydrophilic, hydropobic, or lipophilic group, or pharmaceutically acceptable salts thereof.

In another example of the present invention, the substituted pyrrole adduct can have the following general formula:

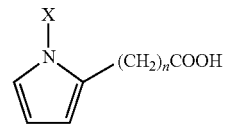

wherein X is a peptide, dipeptide, polypeptide, small molecule, or polymer that includes an amine group that binds to the amine of the substituted pyrrole, and n is an integer from 1-12, or pharmaceutically acceptable salts thereof.

In other embodiments, the substituted pyrrole adduct can include a CEP adduct, a CHP adduct, a CPP adduct, and/or combinations thereof.

It will be appreciated that TLR2 agonists can include other molecules besides substituted pyrroles, such as naturally occurring and/or synthetic peptides. One example of a synthetic peptide that may be used as a TLR2 agonist is $Pam_3CSK_4$. $Pam_3CSK_4$ is a synthetic tripalmitoylated lipopeptide that activates the acylated amino terminus of bacterial lipoproteins. It also activates monocytes and macrophages and is a potent activator of NF-κB. $Pam_3CSK_4$ is recognized by a heterodimer formed between TLR1 and TLR2.

Upon administering a therapeutically effective amount of a TLR2 agonist to the tissue of a subject containing endothelial cells, the TLR2 agonist can bind to TLR2 and thereby activate the TLR2 signaling pathway in a MyD88-dependent manner. Activated MyD88 can then lead to Rac1 activation and integrin expression. Activated endothelial cells can begin to release enzymes (e.g., proteases) that degrade the basement membrane and allow the endothelial cells to escape from the original (parent) vessel walls. The endothelial cells can then proliferate into the surrounding matrix and form solid sprouts connecting neighboring vessels. As sprouts extend toward the source of the angiogenic stimulus, the endothelial cells can migrate in tandem using the integrins. These sprouts can then form loops to become a full-fledged vessel lumen as the endothelial cells migrate to the site of angiogenesis.

The stimulation of angiogenesis can play an important role in a variety of physiological processes, such as embryonic development, wound healing, organ regeneration and female reproductive processes, such as follicle development in the corpus luteum during ovulation and placental growth after pregnancy. Additionally, millions of patients per year in the U.S. suffer from myocardial infarction (MI) and/or critical limb ischemia. Many millions more suffer from related syndromes due to atherosclerosis. Many of these patients will benefit from the ability to stimulate angiogenesis in ischemic areas.

Where a composition comprising the TLR2 agonist is to be used for therapeutic purposes, the dose(s) and route of administration will depend upon the nature of the patient and condition to be treated, and will be at the discretion of the attending physician or veterinarian. Examples of routes that can be used for the administration of the TLR2 agonist include oral, subcutaneous, intramuscular, intraperitoneal or intravenous injection, parenteral, topical application, implants etc.

In one example, a therapeutically effective amount of a pharmaceutical composition comprising the TLR2 agonist can be administered to a wound or an area proximate a wound in a subject to promote healing of the wound. The terms "promoting wound healing" or "promoting healing of wound" can refer to the augmenting, improving, increasing, or inducing closure, healing, or repair of a wound. Wounds treatable by the pharmaceutical compositions described herein that include a TLR2 agonist can include any injury to any portion of the body of a subject (e.g., internal wound or external wound) including: dermal wounds, acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries, such as cuts, incisions, excoriations, injuries sustained as result of accidents, ulcers, such as pressure ulcers, diabetic ulcers, plaster ulcers, and decubitus ulcer, post-surgical injuries. Wounds can also include chronic conditions or wounds, such as pressure sores, bedsores, conditions related to diabetes and poor circulation, and all types of acne. In addition, wounds treatable by the present invention can include dermatitis, such as impetigo, intertrigo, folliculitis and eczema, wounds following dental surgery, periodontal disease, and tumor associated wounds.

The TLR2 agonist can be formulated for either topical and/or local delivery, depending upon the type and severity of the wound. The term "local delivery" can refer to delivery of a pharmaceutical or therapeutic composition to a defined area or region of the body. The term "topical delivery" can refer to delivery of a pharmaceutical or therapeutic composition to a dermal surface (e.g., epidermal) of the body. Topical formulations can include those for delivery via the mouth (buccal) and to the skin such that at least one layer of skin (i.e., the epidermis, dermis, and/or subcutaneous layer) is contacted with a TLR2 agonist.

Formulations for topical administration can include ointments, creams, gels, and pastes comprising a TLR2 agonist to be administered with a pharmaceutically acceptable carrier. Topical formulations can be prepared using oleaginous or water-soluble ointment bases, as is well known to those in the art. For example, such formulations may include vegetable oils, animal fats, and more preferably semisolid hydrocarbons obtained from petroleum. Particular components that may be used can include white ointment, yellow ointment, cetyl esters wax, oleic acid, olive oil, paraffin, petrolatum, white petrolatum, spermaceti, starch glycerite, white wax, yellow wax, lanolin, anhydrous lanolin, and glyceryl monostearate. Various water-soluble ointment bases may also be used including, for example, glycol ethers and derivatives, polyethylene glycols, polyoxyl 40 stearate, and polysorbates.

In one example of the present invention, a TLR2 agonist, such as a CEP adduct can be formulated into a topical formulation (e.g., a cream) for application to, and treatment of, a wound.

A pharmaceutical or therapeutic composition comprising a TLR2 agonist can be applied directly to the wound and/or about the periphery of the wound for a time and at a dosage sufficient to promote angiogenesis at the wound site and thereby facilitate revascularization and closure of the wound. As is well known in the art, dosage for any one subject depends on many factors, including the subject's size, body surface area, age, the particular composition to be administered, sex, time and route of administration, general health, and other drugs being administered concurrently. The specific dosage of a pharmaceutical or therapeutic composition comprising a TLR2 agonist can be readily determined by one skilled in the art.

Upon administration of a pharmaceutical or therapeutic composition comprising a TLR2 agonist to a wound, the TLR2 agonist can bind to TLR2 on an endothelial cell at and/or proximate to the wound site. Binding of the TLR2 agonist to TLR2 can activate the TLR2 signaling pathway in a MyD88-dependent manner and, as described above, lead to Rac1 activation and integrin expression. As activated endothelial cells proliferate into the surrounding matrix and form solid sprouts connecting neighboring vessels, the wound site can become revascularized and the damaged tissue eventually replaced with normal or healthy tissue.

In another example, a therapeutically effective amount of a TLR2 agonist can be administered to ischemic tissue of a subject to treat an ischemic disorder in the subject. Ischemic disorders treatable by the TLR2 agonist can include peripheral vascular disorders, pulmonary emboli, venous thromboses, myocardial infarction, transient ischemic attacks, unstable angina, cerebral vascular ischemia, reversible ischemic neurological deficits, ischemic kidney disease, and stroke disorders. Ischemic disorders can also include iatrogenically-induced ischemic disorders, such as those resulting from a subject undergoing, for example, angioplasty, heart surgery, lung surgery, spinal surgery, brain surgery, vascular surgery, abdominal surgery, kidney surgery, or organ transplantation surgery. Examples of organ transplantation can include heart, lung, pancreas, kidney, and liver translation surgeries.

Ischemic disorders can be treated by administering an amount of a TLR2 agonist to ischemic tissue of subject over a period of time sufficient to promote angiogenesis in the ischemic tissue. For example, the period of time that a TLR2 agonist can be administered to an ischemic tissue may be from about immediately after onset of the ischemic disorder to about days, weeks, or months after the onset of the ischemic disorder.

The TLR2 agonist can be administered directly to or about the periphery of ischemic tissue to promote angiogenesis in, and thus revascularization of, the ischemic tissue. For example, the TLR2 agonist can be delivered to or about the periphery of the ischemic tissue by administering the TLR2 neat or in a pharmaceutical or therapeutic composition. The pharmaceutical or therapeutic composition can provide localized release of the TLR2 to the ischemic tissue (or cells) being treated. Pharmaceutical compositions can generally include an amount of a TLR2 agonist admixed with an acceptable pharmaceutical carrier, such as a sterile aqueous solution, to give a range of final concentrations, depending on the intended use. The techniques of preparation are generally well known in the art as exemplified by *Remington's Pharmaceutical Sciences,* 16th Ed. Mack Publishing Company, 1980, incorporated herein by reference. For human administration, preparations should meet sterility, pyrogenicity, general safety, and purity standards as required by FDA Office of Biological Standards.

By way of example, where the ischemic tissue to be treated is infarcted myocardium, a TLR2 agonist, such as a CEP adduct can be formulated into a pharmaceutical or therapeutic composition for direct injection into the infarcted tissue. For instance, a CEP adduct can be formulated in a unit dosage injectable form (e.g., solution, suspension, and/or emulsion). Examples of pharmaceutical formulations suitable for injection can include sterile aqueous solutions or dispersions, and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), suitable mixtures thereof and vegetable oils. Using a syringe, for example, a therapeutically effective amount of the pharmaceutical or therapeutic composition comprising the CEP adduct can be injected into and/or proximate the infarcted myocardium of the subject. Upon injection, the CEP adduct can bind to TLR2 on an endothelial cell in and/or proximate to the infarcted myocardium. Binding of the CEP adduct to TLR2 can activate the TLR2 signaling pathway in a MyD88-dependent manner and, as described above, lead to Rac1 activation and integrin expression. Activated endothelial cells can then proliferate into the surrounding matrix and form solid sprouts to connect neighboring vessels. The infarcted tissue can become revascularized and eventually replaced with normal or healthy myocardium.

Another aspect of the application can include a method of inhibiting pathological angiogenesis in a subject by administering a therapeutically effective amount of an agent that substantially inhibits complexing of TLR2 with CAP adducts in endothelial cells and/or immune cells of a tissue.

As used herein, the terms "inhibit", "inhibiting" or "inhibition" can include any measurable, reproducible, and/or substantial reduction in: the interaction of CAP adducts and TLR2; angiogenesis; symptoms of diseases or disorders correlated to angiogenesis; or any other activities that complex formation of CAP adducts and TLR2 may mediate. A substantial reduction can include a "reproducible", i.e., consistently observed reduction in complex formation and/or angiogenesis.

In one example, an agent that substantially inhibits complexing of TLR2 with CAP adducts in endothelial cells of a tissue can include a TLR2 antagonist. Generally, TLR2 antagonists can include any substance or molecule that attenuates the effects of a TLR2 agonist. One example of a TLR2 antagonist can include a TLR2 antibody that binds to TLR2 and prevents or inhibits complex formation between CAP adducts and TLR2. Anti-TLR2 antibodies can include whole antibodies, e.g., of any isotype (IgG, IgA, IgM, IgE, etc) and/or fragments thereof that are specifically reactive with a TLR2 epitope. Antibodies can be fragmented using conventional techniques and the fragments screened for utility and/or interaction with a specific epitope of interest. Thus, antibodies and/or fragments thereof can include segments of proteolytically-cleaved or recombinantly-prepared portions of an antibody molecule and/or fragment thereof that is/are capable of reacting with a TLR2 epitope. Non-limiting examples of such proteolytic and/or recombinant fragments can include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. Antibodies and/or fragments thereof can include polyclonal, monoclonal, or other purified preparations of antibodies, recombinant antibodies, monovalent antibodies, and multivalent antibodies. Antibodies and/or fragments thereof may be humanized and further include engineered complexes that comprise antibody-derived binding sites, such as diabodies and triabodies.

In another example, an agent that substantially inhibits complexing of TLR2 with CAP adducts in endothelial cells of a tissue can include any substance or molecule that inhibits the activity and/or formation (e.g., expression) of a CAP adduct, such as a CEP protein adduct. As used herein, the terms "inhibit", "inhibiting" or "inhibition" can include any measurable, reproducible, and/or substantial reduction in: the formation of CAP adducts; the activity of CAP adducts; the interaction of CAP adducts and TLR2; and/or any other pathological activities complex formation of CAP adducts and TLR2 may mediate. An agent that inhibits a CAP adduct can alter CAP adduct activity or CAP adduct formation by a variety of means. The inhibition can be partial or complete inhibition of CAP adduct activity and/or formation. In addition, the agent can inhibit the CAP adduct directly (specifically interact) or indirectly (non-specifically interact).

For example, the agent can inhibit one or more biological activities of a CAP adduct (e.g., a CEP protein adduct). An example of a biological activity of a CAP adduct is angiogenesis. The agent can bind to all or a portion of the CAP adduct (e.g., a portion of the CAP adduct, the CAP portion of the CAP adduct, or the adduct portion of the CAP adduct) under conditions in which the angiogenic activity of the CAP adduct is inhibited.

Alternatively, the agent can inhibit formation of a CAP adduct. The agent can prevent CAP protein adducts from forming by, for example, hydrolyzing CAP protein adducts that have previously formed and thereby regenerating the primary amino group found in the unmodified biomolecule. In one example, the agent can interact with HOHA or its esters, e.g., phospholipid derivatives containing a HOHA acyl group esterified to the sn-2 position, and/or the protein which forms an adduct with HOHA prior to formation of a CEP protein adduct, thereby preventing CEP protein adducts from forming. Alternatively, the agent can interact with an upstream product (e.g., DHA) of the reaction (i.e., leading to formation of CEP protein adducts to prevent CEP protein adduct formation) and/or interact with the CEP protein adduct or portion thereof after CEP protein adducts have formed so that the pyrrole moiety of the CEP and the protein of the CEP protein adduct is disrupted (e.g., the agent can cleave the CEP group from the protein).

Examples of agents that can inhibit receptor-mediated effects of CAP adducts (e.g., CEP protein adducts) can include nucleic acids, fragments or derivatives thereof and vectors comprising such nucleic acids (e.g., a nucleic acid molecule, cDNA, and/or RNA), polypeptides, peptidomimetics, fusion proteins or prodrugs thereof, antibodies, ribozymes, aptamers, small molecules, and other compounds that inhibit CAP adduct activity and/or formation. More specific examples of agents that inhibit CAP adduct activity and/or formation are disclosed in PCT Publication No. WO 2008/013797 A2, the entirety of which is hereby incorporated by reference.

Depending upon the type and severity of the pathological angiogenesis, the agents that substantially inhibit complexing of TLR2 with CAP adducts can be prepared as a pharmaceutical or therapeutic composition (described above) and then administered to the subject via an appropriate route (also described above). Upon administration to the subject, the agent can substantially inhibit complexing of TLR2 with CAP adducts in endothelial cells. In the absence of TLR2 and CAP adduct complexing, the TLR2 signaling pathway will not be activated and, in turn, will not lead to integrin expression by endothelial cells. Without an activated TLR2 signaling pathway, endothelial cells will not proliferate into the surrounding matrix to form solid sprouts connecting neighboring vessels. Consequently, pathological angiogenesis will be substantially prevented or inhibited in the subject.

In accordance with another aspect of the application, the agents that substantially inhibit complexing of TLR2 with CAP adducts may be used to treat animals and patients with aberrant angiogenesis, such as that contributing to a variety of diseases and disorders. The most prevalent and/or clinically important of these, outside the field of cancer treatment, include arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypertrophic scars, oslerweber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the composition described, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Another example of a disease mediated by angiogenesis is occular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases include, but are not limited to, diseases associated with rubeosis and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stipulatory activity. This application provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the compositions described herein. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the compositions described herein in accordance with the knowledge in the art, as disclosed in, e.g., U.S. Pat. No. 5,712,291 (specifically incorporated herein by reference), that unified benefits result from the application of anti-angiogenic strategies to the treatment of angiogenic diseases.

The agents that substantially inhibit complexing of TLR2 with CAP adducts can also be utilized in the treatment of neoplastic disorders, such as tumors or cancers. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs.

The agents that substantially inhibit complexing of TLR2 with CAP adducts described herein are thus broadly applicable to the treatment of any malignant tumor having a vascular component. In using the agents that substantially inhibit complexing of TLR2 with CAP adducts in the treatment of tumors, particularly vascularized, malignant tumors, the agents may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using agents that substantially inhibit complexing of TLR2 with CAP adducts.

Knowledge of the role of angiogenesis in the maintenance and metastasis of tumors has led to a prognostic indicator for cancers, such as breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by the therapies described herein will reduce or negate the recurrence of such tumors.

The compositions described herein can also be used in the treatment of any patient that presents with a solid tumor. In light of the specific properties of the agents that substantially inhibit complexing of TLR2 with CAP adducts, the therapeutics described herein will have reduced side effects. Particular advantages will result in the maintenance or enhancement of host immune responses against the tumor, as mediated by macrophages, and in the lack of adverse effects on bone tissue. The compositions will thus be the anti-angiogenic therapy of choice for the treatment of pediatric cancers and patients having, or at risk for developing, osteoporosis and other bone deficiencies.

Although all malignancies and solid tumors may be treated by the compositions or agents described herein, the agents that substantially inhibit complexing of TLR2 with CAP adducts are particularly contemplated for use in treating patients with more angiogenic tumors, or patients at risk for metastasis.

The compositions and methods described herein also intended as a preventative or prophylactic treatment. These aspects include the ability of the invention to treat patients presenting with a primary tumor who may have metastatic tumors, or tumor cells in the earlier stages of metastatic tumor seeding. As an anti-angiogenic strategy, the compositions and methods may also be used to prevent tumor development in subjects at moderate or high risk for developing a tumor, as based upon prognostic tests and/or close relatives suffering from a hereditary cancer.

Therapeutically effective doses of the agents that substantially inhibit complexing of TLR2 with CAP adducts are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors are widely used in pre-clinical testing.

In using the agents that substantially inhibit complexing of TLR2 with CAP adducts in anti-angiogenic therapies, one can also draw on other published data in order to assist in the formulation of doses for clinical treatment. For instance, although the agents and methods described herein have distinct advantages over those in the art, the information in the literature concerning treatment with other polypeptides can still be used in combination with the data and teaching in the present application to design and/or optimize treatment protocols and doses.

Any dose, or combined medicament of the agents that substantially inhibit complexing of TLR2 with CAP adducts, that results in any consistently detectable anti-angiogenic effect, inhibition of metastasis, tumor vasculature destruction, tumor thrombosis, necrosis and/or general anti-tumor effect. The application may also be effective against vessels downstream of the tumor, i.e., target at least a sub-set of the draining vessels, particularly as cytokines released from the tumor will be acting on these vessels, changing their antigenic profile.

It will also be appreciated that an agent that substantially inhibits complexing of TLR2 with CAP adducts in endothelial cells can be used in combination and adjunctive therapies for treating aberrant angiogenesis (e.g., neoplastic disorders). The phrase "combination therapy" can embrace the administration of the agent that substantially inhibit complexing of TLR2 with CAP adducts, and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" can embrace administration of these therapeutic agents in a sequential manner; that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage having a fixed ratio of each therapeutic agent or in multiple, single dosages for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues.

The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" can also embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" can encompass treatment of a subject with agents that reduce or avoid side effects associated with the combination therapy, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anti-cancer drugs.

In one example, the therapeutic agent administered in combination therapy with the agents described herein can comprise anti-proliferative agents. The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms, such as biological response modification. There are large numbers of anti-proliferative agent agents available in commercial use, in clinical evaluation and in pre-clinical development, which could be used by combination drug chemotherapy. For convenience of discussion, anti-proliferative agents are classified into the following classes, subtypes and species: ACE inhibitors; alkylating agents; angiogenesis inhibitors; angiostatin; anthracyclines/DNA intercalators; anti-cancer antibiotics or antibiotic-type agents; antimetabolites; antimetastatic compounds; asparaginases; bisphosphonates; cGMP phosphodiesterase inhibitors; calcium carbonate; cyclooxygenase-2 inhibitors; DHA derivatives; DNA topoisomerase; endostatin; epipodophylotoxins; genistein; hormonal anticancer agents; hydrophilic bile acids (URSO); immunomodulators or immunological agents; integrin antagonists; interferon antagonists or agents; MMP inhibitors; miscellaneous antineoplastic agents; nitrosoureas; NSAIDs; ornithine decarboxylase inhibitors; pBATTs; radio/chemo sensitizers/protectors; retinoids; selective inhibitors of proliferation and migration of endotheliai cells; selenium; stromelysin inhibitors; taxanes; vaccines; and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Another aspect of the application relates to a method for modulating one or more inflammatory and/or autoimmune diseases or disorders mediated by TLR2 in a subject by administering to the subject a composition comprising an agent that modulates one or more CAP adducts in the subject. Inflammatory and/or autoimmune diseases or disorders can refer to diseases or disorders in which an activity of TLR2 in an immune cell (e.g., microglia, Schwann cells, monocytes, macrophages, dendritic cells, polymorphonuclear leukocytes (PMNs or PMLs), B cells (e.g., B1a, MZ B, B2), and T cells, including Tregs (e.g., CD4+CD25+ regulatory T cells)), a signal transduction pathway of TLR2 in an immune cell, and/or an activity or signal transduction pathway that is mediated by TLR2 in an immune cell is involved. An inflammatory and/or autoimmune disease or disorder mediated by TLR2 can include a disease or disorder where a TLR2 activity or signal transduction pathway in an immune cell can be modulated for treatment of the disease or disorder. Thus, the application can encompass compositions and methods that modulate inflammatory and/or autoimmune diseases or disorders mediated by TLR2 activity in an immune cell and/or a TLR2 signal transduction pathway in an immune cell to provide a therapeutic benefit or therapeutic activity for treatment of the disease or disorder.

Examples of inflammatory diseases or disorders that are mediated by TLR2 and may be treatable can include, but are not limited to, airway inflammation, asthma, autoimmune diseases or disorders, chronic inflammation, chronic prostatitis, glomerulonephritis, Behcet's disease, hypersensitivities, inflammatory bowel disease, reperfusion injury, rheumatoid arthritis, transplant rejection, ulcerative colitis, uveitis, conjunctivitis and vasculitis.

Examples of autoimmune diseases or disorders that are mediated by TLR2 and may be treatable include, but are not limited to, lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barre syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjogren's syndrome, temporal arteritis, vasculitis, vitiligo, vulvodynia and Wegener's granulomatosis.

The agent that modulates one or more CAP adducts in the subject can include any substance or molecule that promotes or inhibits one or more CAP adducts. Prior to administration to the subject, one or more of the agents can be formulated into a pharmaceutical or therapeutic composition by compounding the agent with at least one pharmaceutically acceptable carrier. As discussed above, pharmaceutically acceptable carriers are known in the art and may include any material or materials, which are not biologically or otherwise undesirable, i.e., the material may be incorporated or added into the composition without causing any undesirable biological effects or interacting in a deleterious manner with any of the other components (i.e., the agents) of the composition. As also discussed above, the particular formulation, dosage, and administration route of the agent may depend upon the subject's individual need, such as the particular inflammatory and/or autoimmune disease or disorder from which the subject is suffering.

In one example, the agent that inhibits one or more CAP adducts can include any substance or molecule that inhibits the activity and/or formation (e.g., expression) of a CAP adduct, such as a CEP protein adduct. For example, the agent can inhibit one or more biological activities of a CAP adduct (e.g., a CEP protein adduct). An example of a biological activity of a CAP adduct is inflammation. The agent can bind to all or a portion of the CAP adduct (e.g., a portion of the CAP adduct, the CAP portion of the CAP adduct, or the adduct portion of the CAP adduct) under conditions in which the inflammatory activity of the CAP adduct is inhibited.

Examples of agents that can inhibit receptor-mediated effects of CAP adducts (e.g., CEP protein adducts) can include nucleic acids, fragments or derivatives thereof and vectors comprising such nucleic acids (e.g., a nucleic acid molecule, cDNA, and/or RNA), polypeptides, peptidomimetics, fusion proteins or prodrugs thereof, antibodies, ribozymes, aptamers, small molecules, and other compounds that inhibit CAP adduct activity and/or formation.

In another aspect, a therapeutically effective amount of an agent that inhibits CAP protein adduct activity and/or formation can be administered to a subject suffering from an inflammatory disease, such as Crohn's disease. Crohn's disease is an ongoing disorder that causes inflammation of the digestive tract. In subjects with Crohn's disease, it is believed that immune cells accumulate in the lining of the intestines, producing chronic inflammation, which leads to ulcerations and bowel injury. The agent can include an antibody or fragment thereof (e.g., monoclonal or polyclonal) that binds to all or a portion of one or more CAP protein adducts to inhibit CAP protein adduct activity and/or formation. The agent can be formulated into a pharmaceutical composition and delivered to the subject via an appropriate route (e.g., intravenous injection or direct administration into the bowel). Upon administration to the subject, the agent can inhibit the formation and/or activity of CAP protein adducts by binding to all or a portion of the CAP protein adducts and thereby preventing TLR2:CAP protein adduct complex formation. By inhibiting TLR2:CAP protein adduct complex formation, the TLR2 signaling pathway is not activated, which, in turn, does not lead to cytokine expression and thus chronic inflammation of the bowel.

Another aspect of the application can include a method for modulating one or more inflammatory and/or autoimmune diseases or disorders mediated by TLR2 in a subject by administering to the subject a composition comprising an agent that promotes TLR2 activation in an immune cell of the subject. Agents that promote TLR2 activation can include TLR2 agonists. As described above, TLR2 agonists can generally include any substance or molecule that binds to TLR2 present on immune cells and induces a response in the immune cells. For example, binding of a TLR2 agonist to TLR2 can promote cytokine expression (e.g., tumor necrosis factors and interleukins) in an immune cell. Examples of TLR2 agonists can include CAP adducts (e.g., CEP protein adducts) and $Pam_3CSK_4$.

In one example of the application, a therapeutically effective amount of a TLR2 agonist (e.g., a CEP protein adduct) can be administered to subject suffering from a bacterial infection. At least one CEP protein adduct can be formulated into a pharmaceutical composition and then delivered to the subject via an appropriate route (e.g., intravenous administration). Upon administration to the subject, a CEP protein adduct can bind to TLR2 on immune cells and thereby activate the TLR2 signaling pathway. Activation of the TLR2 signaling pathway can promote expression of various cytokines by the immune cells (e.g., tumor necrosis factors and interleukins) and lead to an increased inflammatory response (e.g., fever) in the subject, which can subsequently promote clearance of the bacterial infection.

Another aspect of the application relates to a method for treating a dermatological disorder in a subject by administering a therapeutically effective amount of a composition comprising an agent that promotes or inhibits TLR2 activation. Dermatological disorders can include any disorder of skin, hair, or glands. A dermatological disorder can be manifest in the form of visible lesions, pre-emergent lesions, pain, sensitivity to touch, irritation, inflammation, or the like. Dermatological disorders can include disorders of the cutaneous and pilosebaceous unit or the process of keratogenesis. For example, a dermatological disorder can be a disorder of the epidermis or dermis, or within and surrounding a pilosebaceous unit, which is located within the epidermis, dermis, subcutaneous layer, or a combination thereof. Examples of dermatological disorders include, but are not limited to, acne, alopecia, psoriasis, seborrhea, ingrown hairs and pseudofolliculitis barbae, hyperpigmented skin, cutaneous infections, lichen planus, Graham Little Syndrome, periorificial dermatitis, rosacea, hidradenitis suppurativa, dissecting cellulitis, systemic lupus erythematosus, discoid lupus erythematosus, and the like.

Agents that promote TLR2 activation are described above and can include TLR2 agonists, for example, a CAP adduct, such as a CEP adduct.

Agents that inhibit TLR2 activation are also described above and can include, for example, TLR2 antagonists, such as TLR2 antibodies, or an agent that inhibits one or more CAP adducts.

Depending upon the particular dermatological disorder, the agent that promotes or inhibits TLR2 activation can be formulated into a pharmaceutical or therapeutic composition by compounding the agent with at least one pharmaceutically acceptable carrier. As discussed above, pharmaceutically acceptable carriers are known in the art and can include any material or materials which are not biologically or otherwise undesirable, i.e., the material may be incorporated or added into the composition without causing any undesirable biological effects or interacting in a deleterious manner with any of the other components (i.e., the agents) of the composition. As also discussed above, the particular formulation, dosage, and administration route of the agent may depend upon the subject's individual need, such as the particular dermatological disorder from which the subject is suffering.

One example of the application can include a method for treating a dermatological disorder, such as alopecia in a subject by administering to follicle cells of the subject a therapeutically effective amount of a TLR2 agonist that promotes hair growth in the subject. "Alopecia" can refer to partial or full baldness, hair loss, and/or hair thinning, as well as primary cicatricial alopecia (CA), which can refer to a group of hair disorders that cause permanent destruction of the hair follicle. CAs can be classified as lymphocytic, neutrophilic, and combinations thereof (i.e., "mixed"). Examples of lymphocytic CAs can include lichen planopilaris, frontal fibrosing alopecia, chronic cutaneous lupus, erythematosus, pseudopelade, central centrifugal alopecia, alopecia mucinosa, and keratosis follicularis spinulosadecalvans. Examples of neutrophilic CAs can include folliculitis decalvans, tufted folliculitis, and dissecting cellulitis. Examples of mixed CAs can include follicullitis keloidalis and erosive dermatosis.

In a subject suffering from alopecia (e.g., baldness), a TLR2 agonist, such as a CAP adduct can be formulated into a topical formulation. For example, the CAP adduct can be formulated into an ointment, cream, gel, paste, and/or oleaginous or water-soluble ointment base. After formulating the CEP adduct, a therapeutically effective amount of the topical formulation can be applied to the scalp of the subject. As illustrated in FIGS. 12-15, the number of hair follicles is increased upon application of CAP adducts. Administration of a therapeutically effective amount of a pharmaceutical or therapeutic composition comprising a CAP adduct to a subject suffering from alopecia (e.g., baldness) can thus lead to an increase in the number of hair follicles and thereby promote hair growth.

The following example is for the purpose of illustration only and is not intended to limit the scope of the claims, which are appended hereto.

EXAMPLE 1

Materials and Methods
Animal Studies

Wild type C57BL/6 and DsRed transgenic mice were obtained from Jackson Laboratory, $CD36^{-/-}$ from Dr. M. Febbraio (Cleveland Clinic), $SR-B1^{-/-}$ from Dr. M. Kruger, $MyD88^{-/-}$ and $TLR2^{-/-}$ from Dr. S. Akira (Osaka University). All mice were maintained in the Biological Resources Unit of the Lerner Research Institute, accredited by the Association for the Assessment and Accreditation of Laboratory Animal Care International. All experimental work was conducted in compliance with the Institutional Animal Care and Use Committee program.

Immunohistochemistry and Image Analysis

For immunofluorescence staining, we used rabbit polyclonal anti-CEP (described in Crabb, J. W. et al., *Proc Natl Acad Sci USA* 99(23):14682-14687, 2002), anti-CD31 (BioLegend), anti-αSMA (Rockland). We fixed 7 μm thick tissue sections with 4% paraformaldehyde and embedded in paraffin or in OCT freezing medium. After incubation with primary antibodies, samples were washed with PBS and exposed to a Alexa Fluor-labeled secondary antibody, either goat anti-rabbit Alexa Fluor488, anti-rat Alexa Fluor568, or anti-mouse Alexa Fluor568 (Invitrogen). The slides were mounted with medium (DakoCytomation) and images were taken by either a TCS-SP (Leica) or a ZMZ1000 (Nikon) microscope. For quantification, the images were analyzed with ImagePro software (MediaCybernetics).

Bone Marrow Transplant (BMT) and Wound Assay

We performed BMT as previously described (Chen et al., *Nat Med.* 11(11):1188-1196, 2005). Briefly, we subjected two month old male wild type or $TLR2^{-/-}$ mice to irradiation with a total dose of 9 Gy followed by bone marrow reconstitution by tail vein injection with $10^7$ bone marrow cells isolated from donor femurs. 8 weeks after BMT, mice were used for wound healing assays. A back punch wound healing model was used as described elsewhere (Feng, W. et al., *J Cell Biol.* 183(6):1145-1157, 2008). Mice were given PBS or CEP-dipeptide peritoneal injections (1.4 μg per mg of body weight) at the time of injury and on days 2, 4, and 6.

Aortic Ring Assay

The mouse aortic ring assay was performed as previously described (Mahabeleshwar, G. H. et al., *Methods Mol Med.* 129:197-208, 2006).

Isolation of Endothelial Cells

Mouse lungs were excised, minced, and digested using a collagenase-dispase reagent (Roche Diagnostic). Digests were strained and the resulting cell suspension was plated on flasks coated with 1 mg/ml fibronectin. Thereafter, endothelial cells were isolated and characterized as described previously (Mahabeleshwar, G. H. et al., *Methods Mol Med.* 129:197-208, 2006).

Cell Adhesion

We performed cell adhesion assays as described elsewhere (Byzova, T. V. et al., *J Cell Biol.* 143(7):2081-2092, 1998). Briefly, $10^4$ HUVEC or MLEC cells were added to ligand coated wells of a 96-well plate and incubated for 1 h in the presence of CEP-adduct or VEGF as indicated. The cells were washed with and fixed with 4% paraformaldehyde in PBS. Thereafter cells were contrasted by hematoxylin staining and photographs were taken.

Cell Migration Assay

We used fibronectin-coated transwell inserts of 8 μm pore size (Corning). HUVEC or MLEC cells were added into each well. The lower chamber was complemented with an attractant as indicated. Cells were allowed to migrate for 5 h and fixed with 4% paraformaldehyde for 20 min then stained with hematoxylin. The photographs of 4 random fields were taken using a phase contrast inverted microscope (Athena).

Tube Formation Assay

HUVEC or MLEC cells were seeded on Matrigel-coated plates (BD Bioscience). Medium was supplemented with VEGF or protein adducts as indicated, and cells were further incubated at 37° C. for 8 h. Tube formation was observed using a phase contrast inverted microscope, and photographs were taken from each well. The data were quantified by measuring the length of tubes with ImagePro software.

Hind Limb Ischemia Model

The femoral artery was ligated near the caudally branching deep femoral artery and a second ligation was placed in proximity of the tibial arteries branching. The portion of the artery and vein between the ligation points was excised. Hind-limb blood flow was measured by a laser Doppler moorLDI2-IR near infrared laser Class 3R (Moor Instruments) in arbitrary perfusion units (PU). The results were plotted as a ratio of surgery to nonsurgery leg for each animal to account for variations between animals.

Rac1 Activation Assay

Per assay, we used $2 \times 10^6$ cells lysed in 500 µl buffer: 25 mM HEPS KOH pH 7.5; 250 mM NaCl, 1% NP-40, 10% glycerol, 10 mM $MgCl_2$ 2 mM EGTA. GST-PAK-PBD pre-absorbed on glutathione agarose beads (Cytoskeleton) was added in the amount of 20 µl 50% slurry followed by incubation on a rotary shaker for 45 min at 4° C. Beads were washed four times with lysis buffer before elution with SDS-PAG sample buffer. Rac 1 was detected by Western Blot (clone 102, BD Bioscience).

Luciferase Reported Assay

We transfected HEK 293 cells by hTLR2 expression plasmid (InvivoGen) or control vector, as well as NF-kB luciferase reporter (gift from Dr. P. Chumakov, Cleveland Clinic). 24 hrs post-transfection cells were exposed to CEP adduct or the carrier protein for an additional 8 hrs. Reporter activity test was performed with a luciferase assay system (Promega) and the readout was normalized to the protein amount.

Elisa

We immobilized 2 µg CEP-KLH or KLH on a 96-well polystyrene plate (Thermo Labsystems) overnight at 4° C. and blocked with 5 mg/ml BSA on PBS, followed by a wash with 1 mg/ml BSA. We added the indicated amounts of recombinant TLR2 extracellular domain (R&D Systems) for 4 h at room temperature then washed the plates. Detection was done with anti-TLR2 antibodies (clone TL2.1, eBioscience) and anti-mouse HRP-coupled antibodies (Bio-Rad)); quantitation was done by a colorimetric assay (R&D Systems) at 560 nm using a Vmax plate reader (Molecular Devices).

Statistical Analysis

All data are presented as mean±s.e.m. for all studies. Probability values were based on the paired t test: NS—not significant, *$P<0.05$, $P<0.01$, *$P<0.001$.

Results/Discussion

As shown in FIG. 1, the adducts, CEP in particular, can be detected during the wound healing process in a transient fashion. The levels of CEP increase dramatically in 5 day old wounds compared to normal skin and return to their original levels when the wound is completely healed (in 28 days) (FIG. 1A). This increase coincides with the recruitment of bone marrow derived cells (FIG. 1B), which contribute to oxidation by means of respiratory burst (Segal, A. W. *Annu Rev Immunol*. 23:197-223, 2005). Based on co-staining, it appears that F4/80+ macrophages but not Gr-1+ neutrophils accumulate CEP (FIG. 1C). Importantly, high levels of CEP are apparent at the stage of intense wound vascularization as evidenced by CD31 and CEP co-staining, suggesting a possible role for this adduct in wound angiogenesis (FIG. 1A). In contrast to the transient presence of CEP during the wound healing process, its levels were continuously high in pathological specimens. In a mouse model of melanoma, a tumor characterized by excessive vascularization with a substantial inflammatory component, intensity of CEP staining is ~9 times higher than in normal uninjured skin (FIG. 1D). Likewise, CEP was present at higher levels in human melanoma specimens compared to normal skin from the same donor (FIG. 1E). In uninjured muscle tissue, CEP is often present within the vascular wall and is colocalized with the SMA layer of arterioles (FIG. 1F). Remarkably, the intensity of CEP staining increased substantially with aging (FIG. 1G), possibly reflecting accumulation of oxidative products over time. Taken together, these results suggest that the end products of lipid oxidation, represented by CEP might serve as important regulators of inflammation-associated vascularization.

Figure 2:
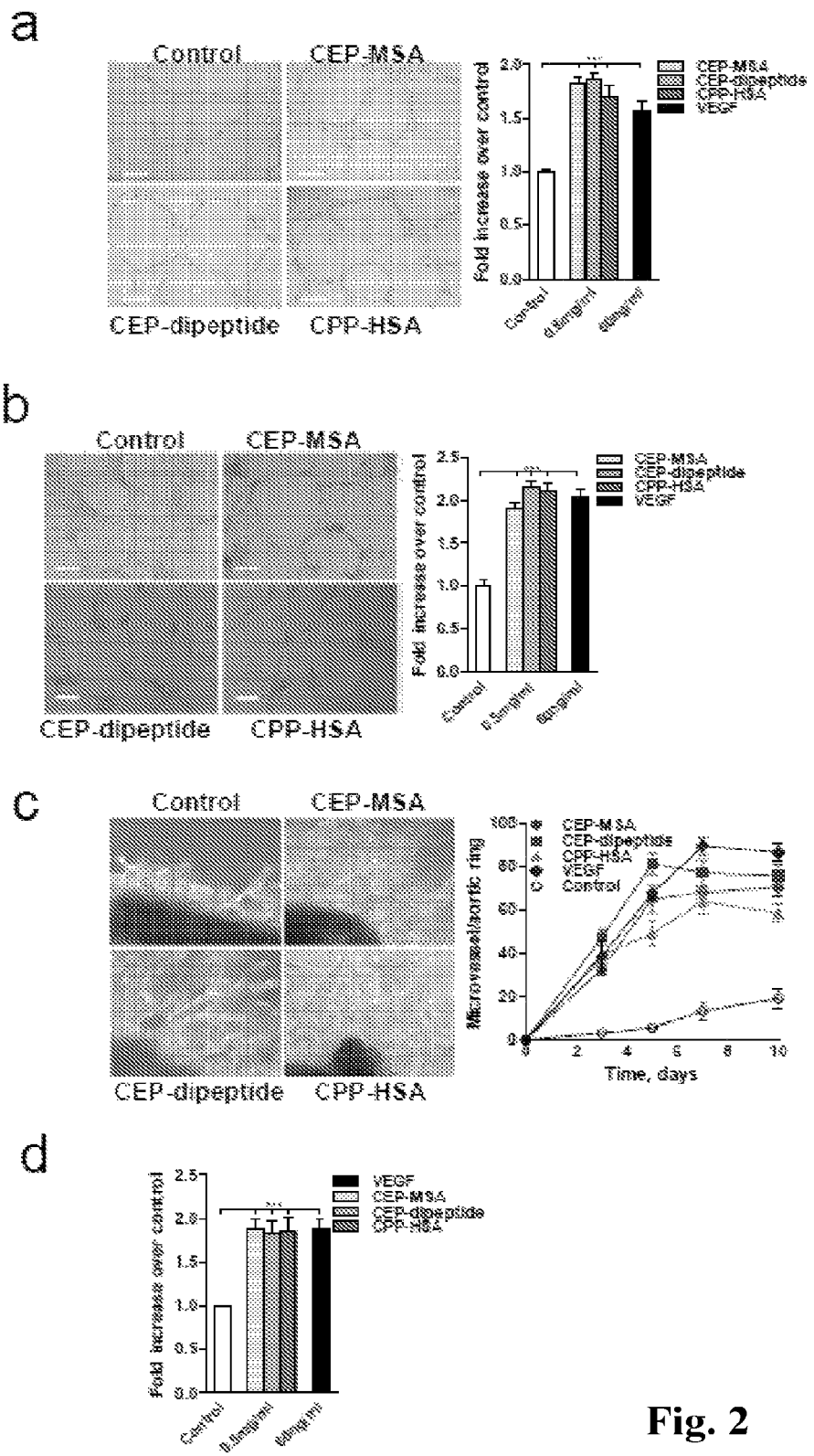
FIGS. 2A-H are a series of micrographs showing that the pro-angiogenic effect of oxidized adducts is not restricted to a particular type of endothelial cell and is independent of CD36 and SR-B1 expression.
Figure 2:
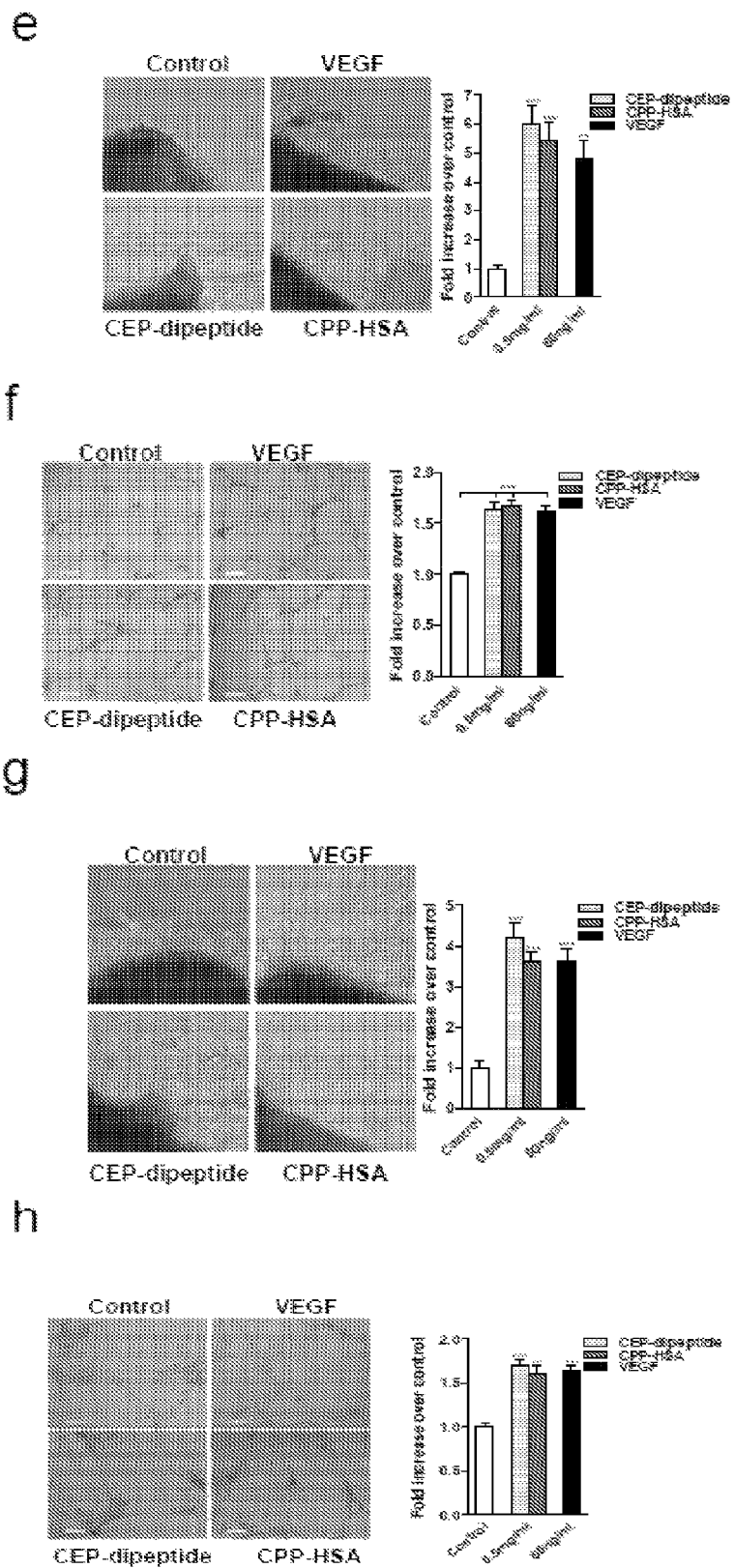
Figure 5:
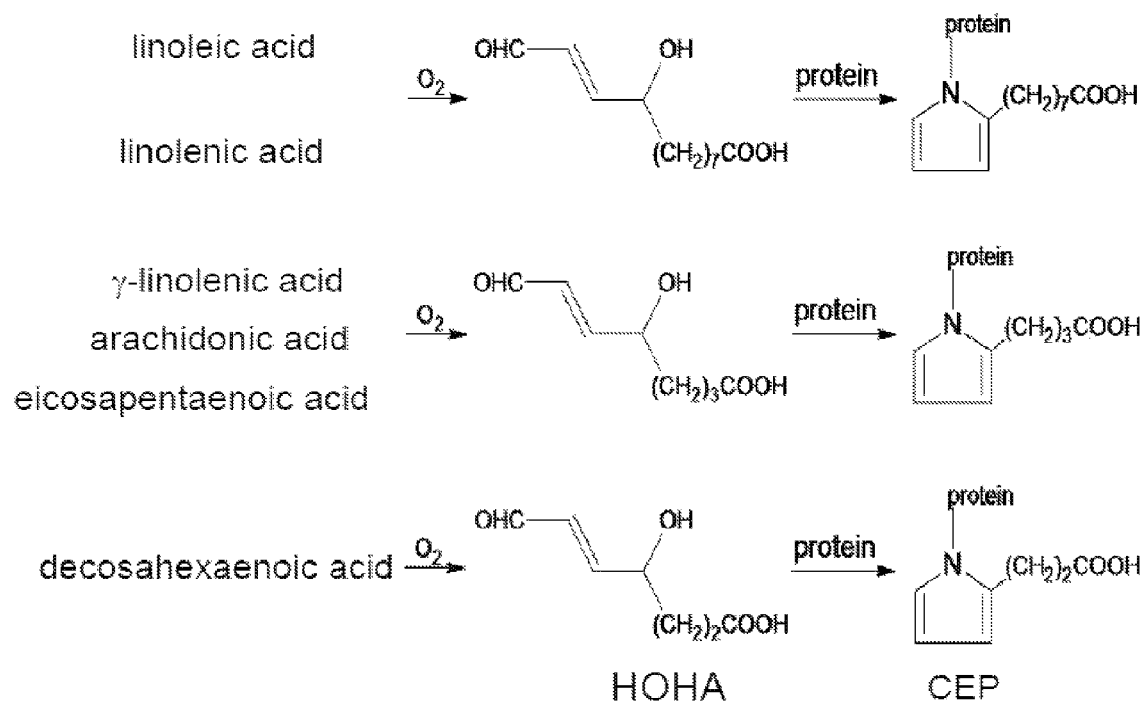
FIG. 5 is a schematic diagram of CAP protein adduct biogenesis.

Indeed, as shown in FIG. 2, CEP directly promotes angiogenic responses of isolated endothelial cells of various origins. When tested on HUVEC, mouse lung (MLEC), or mouse aortic endothelial cells (MAEC), the pro-angiogenic effect of CEP was comparable to that of VEGF, as assessed by tube formation (FIGS. 2A-B), aortic ring (FIG. 2C) and cell migration assays (FIG. 2D). The protein moiety did not influence CEP's effect, as adducts coupled to MSA, HSA or a dipeptide were equally effective in promoting angiogenic responses (FIGS. 2A-D). Similar to VEGF, the effect of CEP was integrin dependent (FIG. 6A). However, in contrast to VEGF, stimulation of endothelial cells with CEP did not result in VEGFR2 phosphorylation (FIG. 6B). Thus, CEP is able to activate proangiogenic responses of isolated endothelial cells by a mechanism independent of VEGF/VEGFR2 signaling. Importantly, adducts from the same family of CAP (FIG. 5) represented by CPP (carboxypropylpyrrole) were also pro-angiogenic (FIGS. 2A-H), implying that the EC recognize and respond to the structural pattern rather than to a particular chemical moiety.

To address the nature of the possible receptor mediating CEP-induced angiogenesis, we considered the role of scavenger receptors which are capable of pattern recognition. We assessed angiogenic responses to CEP and CPP adducts using EC from $CD36^{-/-}$ and scavenger receptor B1 ($SR-B1$)$^{-/-}$ mice. Both adducts promoted endothelial sprouting (FIG. 2E) and tube formation (FIG. 2F) of $CD36^{-/-}$ EC and were as effective simulators as VEGF. Likewise, ablation of the functionally similar SR-B1 receptor had no substantial impact on EC responses to CEP and CPP (FIGS. 2G-H) indicating that scavenger receptors are not involved in recognition of these adducts.

Figure 3:
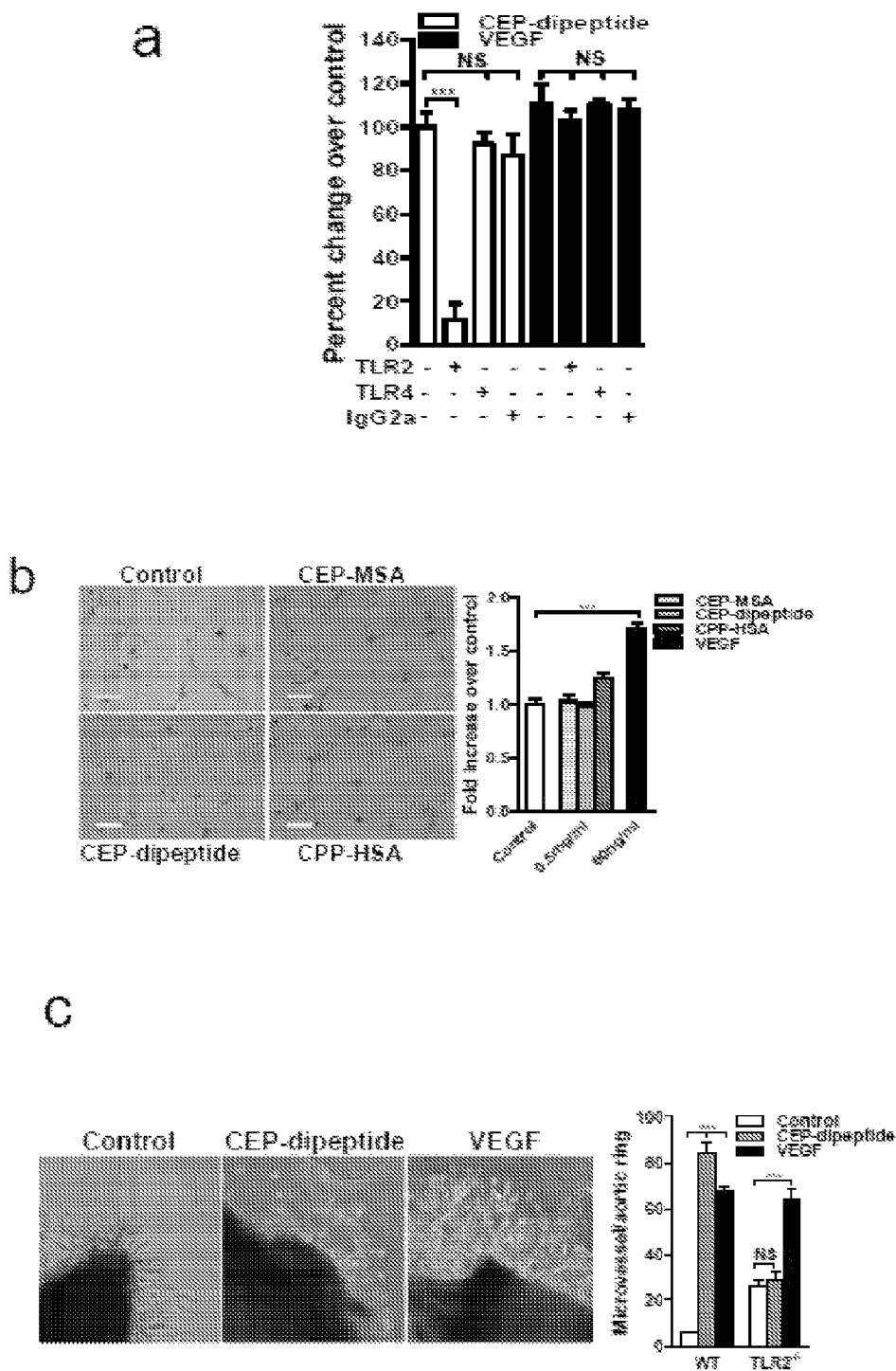
FIGS. 3A-F shows that angiogenesis induced by oxidized lipid products is mediated by toll-like receptor 2 (TLR2).
Figure 3:
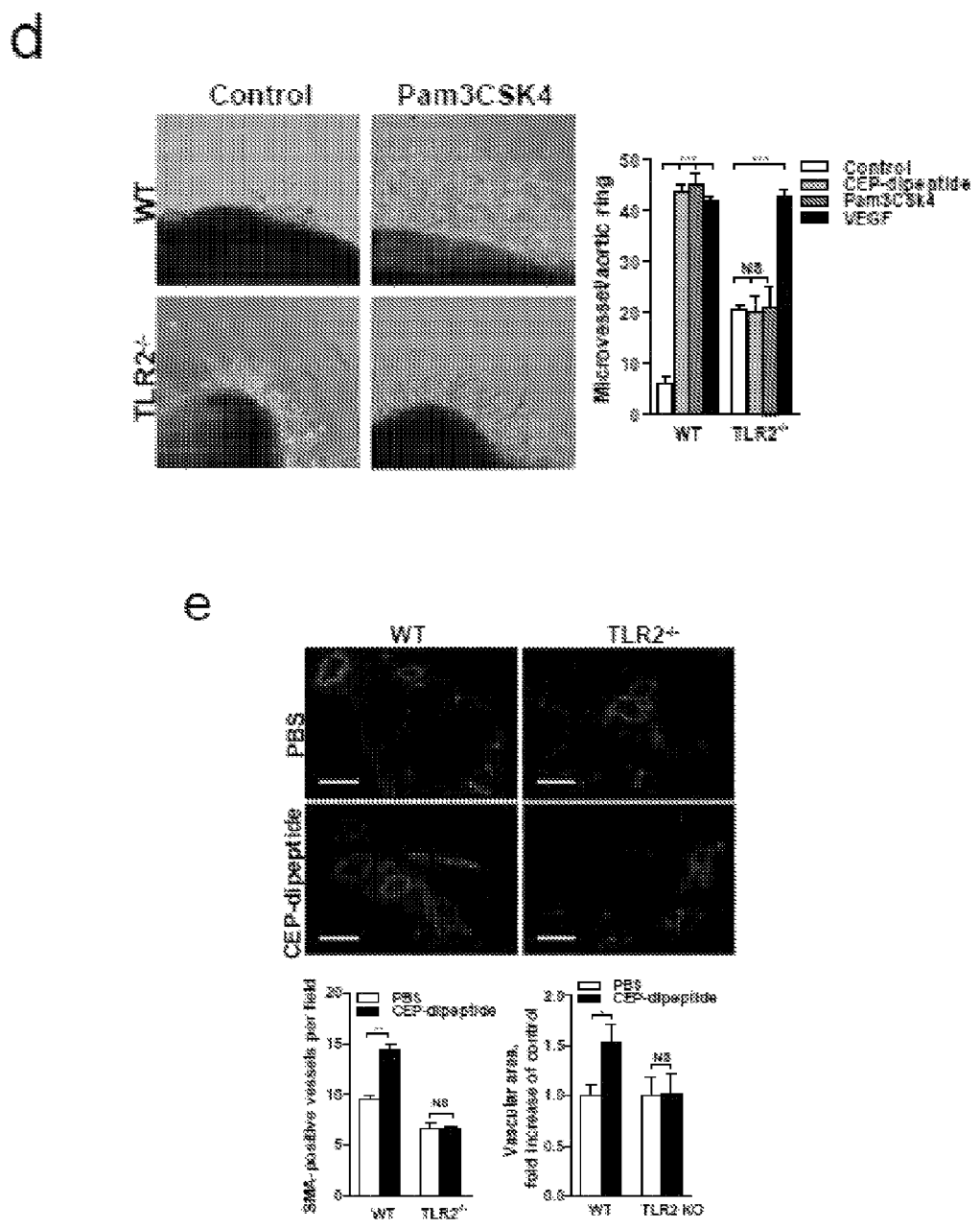
Figure 3:
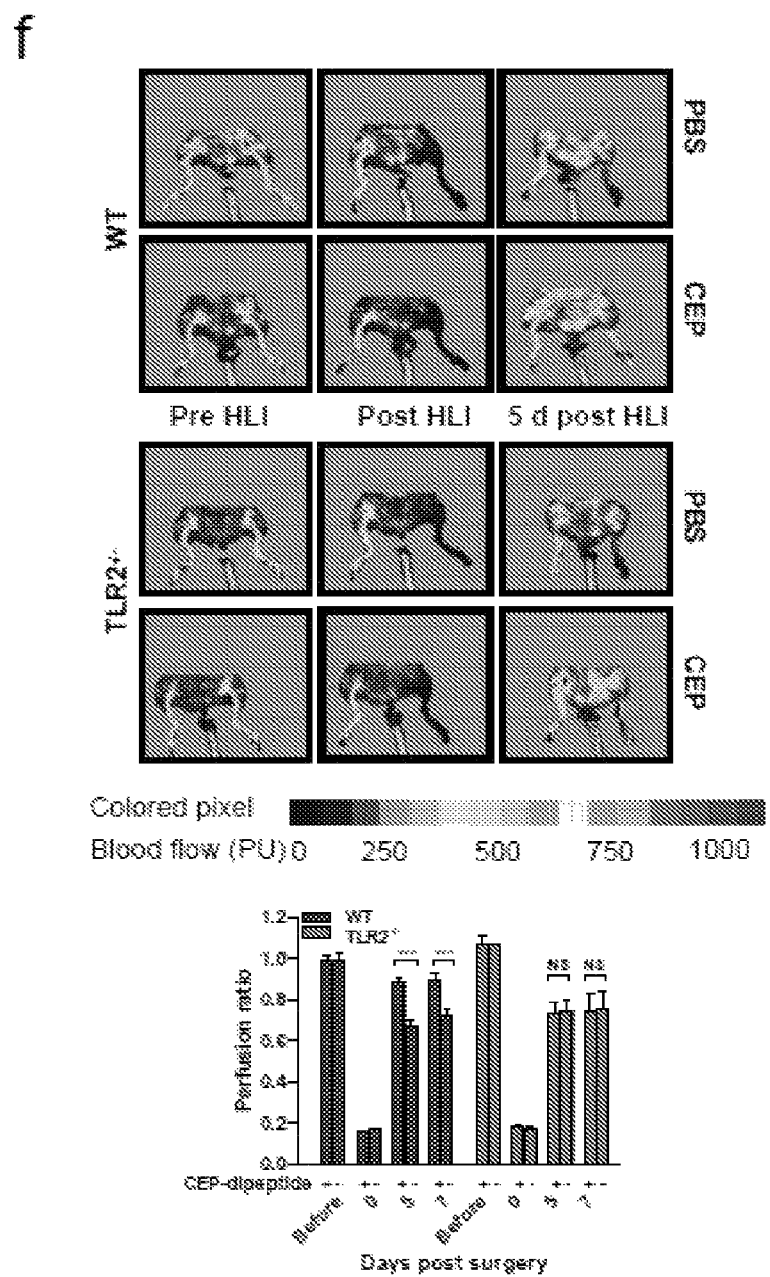
Figure 7:
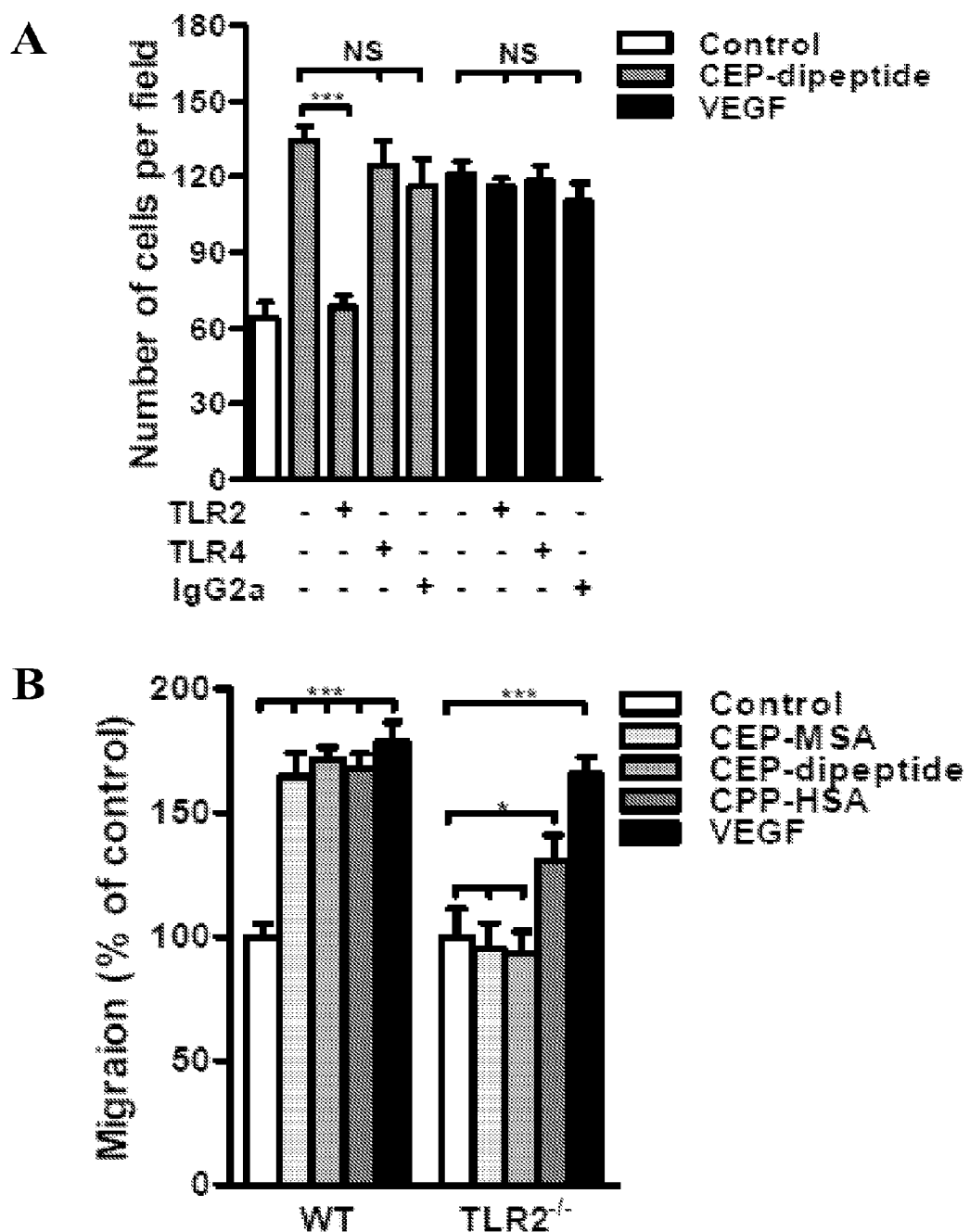
FIGS. 7A-D are a series of graphs showing that: CEP-induced responses are TLR2 dependent (FIG. 7A); migration of MLEC cells in response to the indicated protein adducts is dependent on TLR2 expression (FIG. 7B); HUVEC tube formation in response to $Pam_3CSK_4$ is inhibited by TLR2 blocking antibodies but not isotype control antibodies (FIG. 7C); and HUVEC response to $Pam_3CSK_4$ is TLR2 dependent.

Since EC appear to respond to CAPs molecular pattern and the presence of this pattern is a characteristic of oxidative stress, we hypothesized the involvement of Toll like family receptors (TLRs). Of all TLRs, we focused on TLR2 and TLR4, since they are expressed on endothelium and known to recognize a broad range of pathogen-derived and endogenous ligands, both of lipid and protein nature (Zahringer, U. et al., *Immunobiology* 213(3-4):205-224, 2008). As shown in FIG. 3A, blocking antibodies against TLR2 but not TLR4 specifically inhibit CEP- but not VEGF-induced endothelial tube formation. Similar results were observed in EC migration assays (FIG. 7A). To further address the role of TLR2 in CEP-driven angiogenesis, EC from $TLR2^{-/-}$ mice were compared to those from TLR2$^{+/+}$ controls. As shown in FIG. 3, TLR2$^{-/-}$ EC did not respond to CEP or CPP treatment in either tube formation or aortic ring sprouting assays (FIGS. 3B and 3C, respectively). At the same time, VEGF-triggered EC responses were not affected by the lack of TLR2 (FIGS. 3B-C). Similar results were observed in cell migration assays (FIG. 7B). To confirm the key role of TLR2 in pro-angiogenic responses of EC, the TLR2 synthetic ligand Pam3CSK4 (Aliprantis, A. O. et al., *Science* 285(5428):736-739, 1999) was tested under similar conditions. The ligand induced robust sprouting of EC from aortic rings of TLR2$^{+/+}$ but not TLR2$^{-/-}$ mice (FIG. 3D). Likewise, in two other functional assays, EC tube formation and EC adhesion, Pam3CSK4 was as effective a stimulator as CEP or VEGF. The blockade of TLR2 using antibodies inhibited the effect of Pam3CSK4, but not VEGF (FIGS. 7c-D). Therefore, activation of endothelial TLR2 by CEP or by its synthetic ligand promotes angiogenic responses which are VEGF independent.

Figure 8:
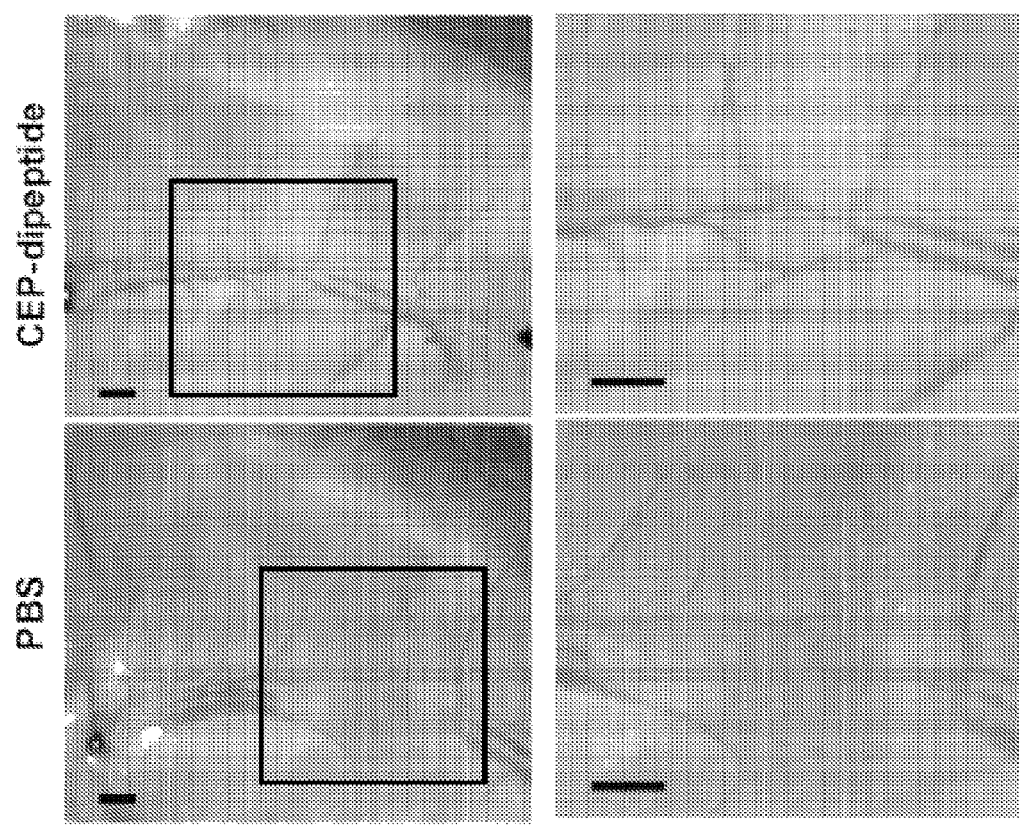
FIG. 8 is a series of images of a ligated femoral artery (post-operation day 28, CEP or vehicle only intramuscular injection as indicated) (scale bar 150 μm; right—magnified view of the area indicated on the left)

Having established the role of TLR2 in the proangiogenic effect of CEP in vitro, we considered the possibility that exogenous CEP might promote vascularization in vivo. In the hind limb ischemia model, CEP injections enhanced tissue revascularization after ligation surgery. As shown in FIG. 3E, CEP stimulated an increase in vascular density, as assessed by the number of SMA-positive vessels per field, as well as an increase in average vascular area. These proangiogenic effects were dependent on TLR2 since TLR2$^{-/-}$ mice were not responsive to exogenous CEP and exhibited substantially impaired revascularization (FIG. 3E). As a consequence, CEP injection resulted in the stimulation of blood flow in TLR2$^{+/+}$ but not TLR2$^{-/-}$ mice (FIG. 3F). The enhanced blood flow was due to increased angiogenesis (FIG. 3E) and, possibly, to the restructuring of collateral blood vessels bypassing the ligation of the femoral artery (FIG. 8).

Figure 4:
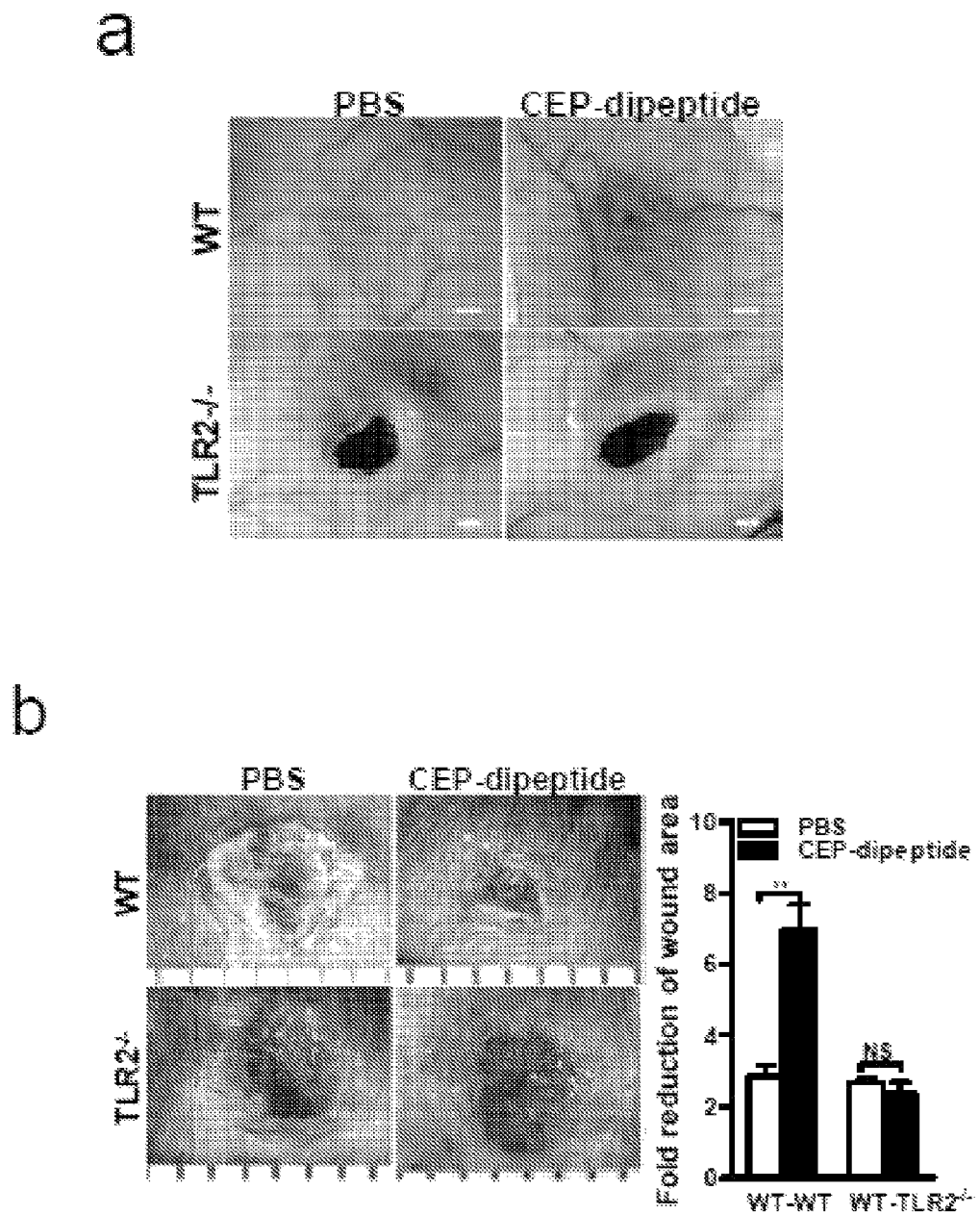
FIGS. 4A-E show wound angiogenesis in $TLR2^{+/+}$ and $TLR2^{-/-}$ mice before and after bone marrow transplantation, and the role of Myd88 and Rac1.
Figure 4:
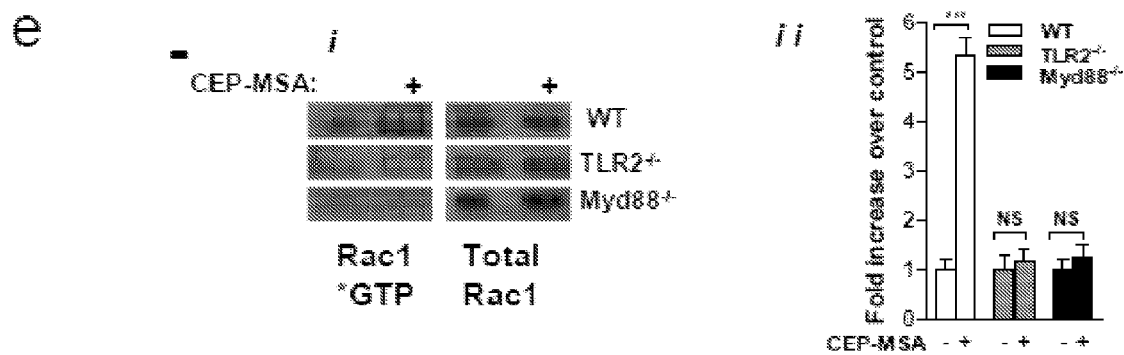

Since CEP synthesis is a common phenomenon in wound healing (FIGS. 1A-C), we addressed the role of this adduct in wound vascularization. To distinguish the effect of CEP on EC from that on inflammatory cells, TLR2$^{-/-}$ mice were transplanted with TLR2$^{+/+}$ bone marrow. The resulting TLR2$^{+/+}$>TLR2$^{-/-}$ and TLR2$^{+/+}$>TLR2$^{+/+}$ chimeras were used for wound assays. CEP injection into TLR2$^{+/+}$>TLR2$^{+/+}$ animals resulted in augmented vascularization and more than three-fold faster wound closure when compared to the PBS-treated group (FIGS. 4A-B). At the same time, the wounds of TLR2$^{+/+}$>TLR2$^{-/-}$ animals healed substantially slower, and CEP had no effect on either wound closure or vascularization in these mice (FIGS. 4A-E). Quantification of the vasculature in the wounded tissue revealed a 2.5-fold increase in vascular area and a 1.7-fold increase in vascular density resulting from CEP treatment compared to PBS treatment (FIG. 4C). The lack of TLR2 on non-hematopoietic cells completely abrogated proangiogenic activity of CEP (FIG. 4C), indicating the key role for this receptor. Together with the results of experiments on isolated endothelial cells, these data show that TLR2 on vascular but not on immune cells is responsible for recognition of the end-products of lipid oxidation and initiation of proangiogenic signaling.

Figure 9:
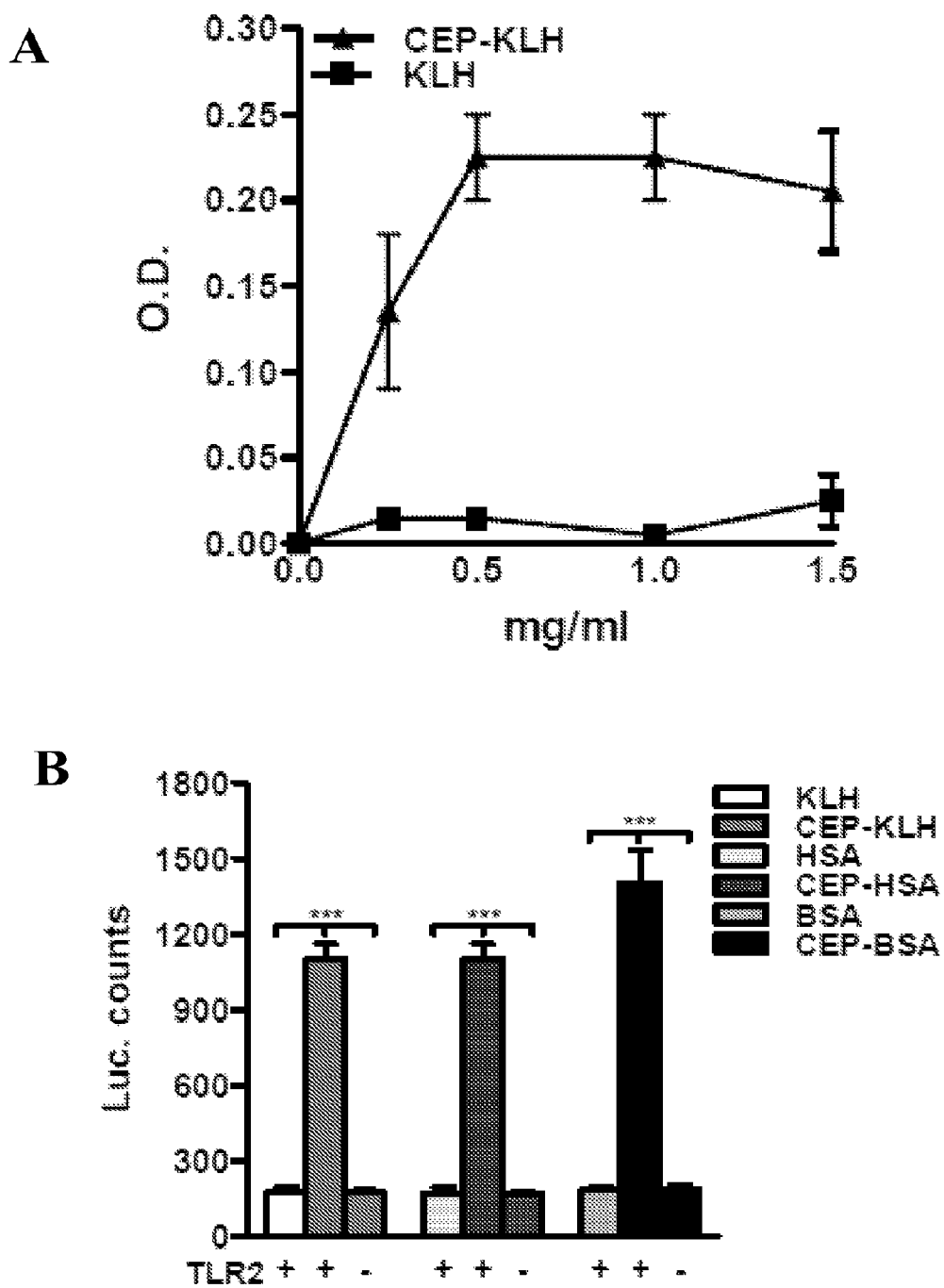
FIGS. 9A-B are a series of plots showing TLR2 recombinant protein binding to CEP-KLH adduct over a range of TLR2 protein concentrations (FIG. 9A) (KLH protein is shown for comparison; optical density ±s.e.m., n=3), and Luciferase reporting assay for NF-κB activation (FIG. 9B) (TLR2 or empty vector transfection shown on bottom) (Luciferase counts ±s.e.m., n=3, ***P<0.001)
Figure 10:
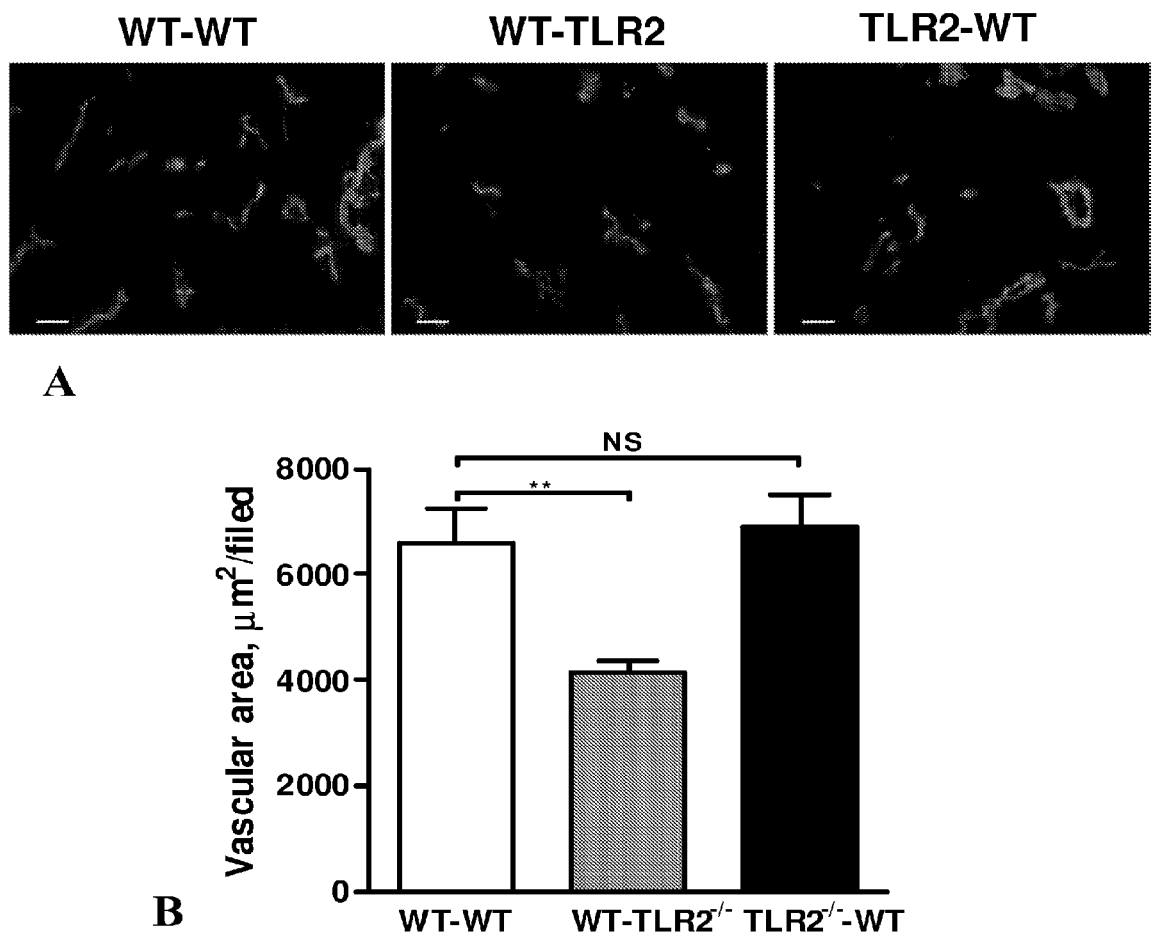
FIGS. 10A-B show tumor vasculature (melanoma) in TLR2$^{-/-}$ mice with WT bone marrow compared to WT mice transplanted with TLR2$^{-/-}$ bone marrow.
Figure 11:
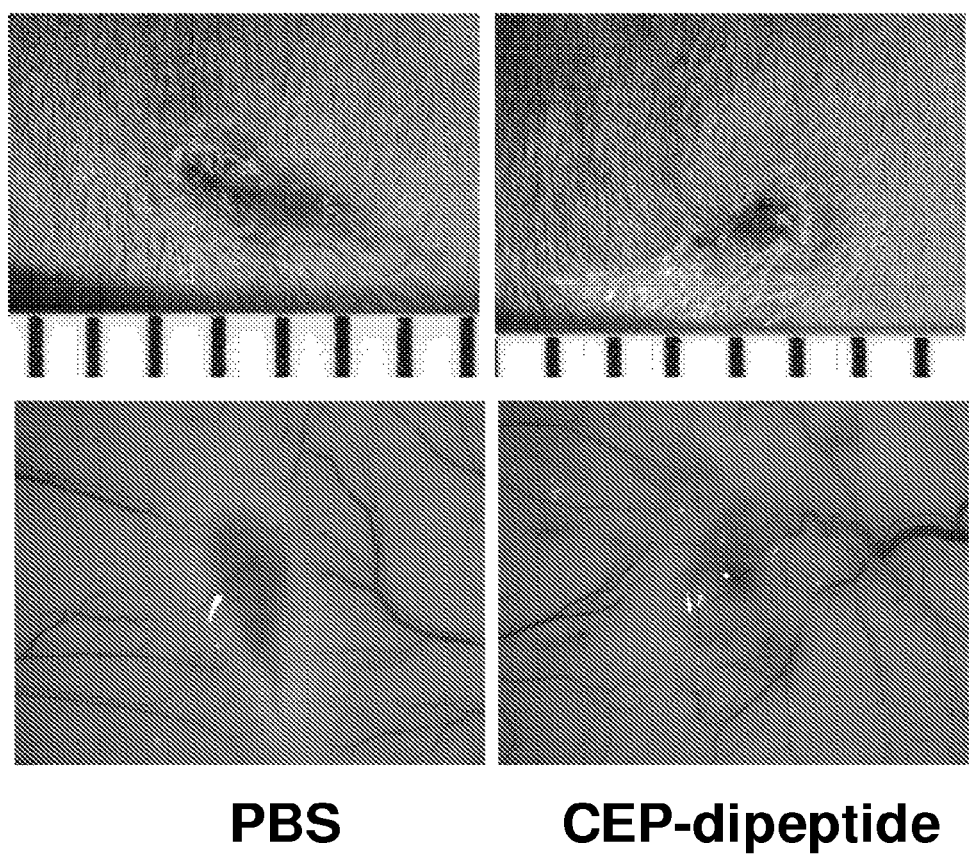
FIG. 11 is a series of images showing a wound assay with white petrolatum CEP-dipeptide added topically (note increased vascularization on the right, CEP application)

The key mechanism underlying broad ligand specificity of TLR2 (Zahringer, U. et al., *Immunobiology* 213(3-4):205-224, 2008) is its heterodimerization with other members of the TLR family (Ozinsky, A. et al., *Proc Natl Acad Sci USA* 97(25):13766-13771, 2000) and its ability to form complexes with heterologous co-receptors (Hoebe, K. et al., *Nature* 433(7025):523-527, 2005). Thus, it is possible that recognition of oxidized lipids might require a co-receptor for TLR2. However, when tested in ELISA, recombinant TLR2 bound the CEP protein adduct, but not the carrier protein alone, indicating the possibility of a direct interaction between CEP and TLR2 (FIG. 9A). Importantly, similar to other established ligands for TLR2, CEP triggers a major TLR signaling event, NF-kB activation. As shown in NF-kB luciferase reporter assay, CEP induced NF-kB activation and TLR2 was required for this response (FIG. 9B).

Next, we considered whether MyD88 adapter protein, a known mediator of TLR2 signaling, is involved in proangiogenic activity of CEP. As shown in FIG. 4D, CEP-induced EC sprouting is MyD88-dependent since MyD88$^{-/-}$ cells did not respond to stimulation by CEP. At the same time, VEGF-induced angiogenesis was not affected by the lack of MyD88 (FIG. 4D). Considering that CEP-induced angiogenic responses are integrin dependent, we focused on mediators common for integrin and TLR signaling. Rac1 small G protein is a key regulator of integrin-mediated migration (Tan, W. et al., *FASEB J.* 22(6):1829-1838, 2008), which is known to function in vascular development, and, most interestingly, is reported to be activated downstream of TLR (Arbibe, L. et al., *Nat Immunol.* 1(6):533-540, 2000). Accordingly, we assessed Rac1's GTP load in response to CEP treatment as a measure of pro-migratory signaling induced by the compound. As shown in FIG. 4E, Rac1's GTP-bound form is readily detected after CEP treatment of TLR2$^{+/+}$, but not TLR2$^{-/-}$ or MyD88$^{-/-}$ cells. Thus, lipid oxidation products, represented by CEP, promote angiogenic responses of EC by activating the TLR2 signaling pathway in a MyD88-dependent manner, leading to Rac1 activation which, in turn, facilitates integrin function.

These findings demonstrate the presence of a novel mechanism of angiogenesis which is independent of hypoxia-triggered VEGF expression. In this model, the products of lipid oxidation are generated as a consequence of inflammation, recruitment of myeloid cells, and respiratory burst. These products are directly recognized by TLR2 on EC and promote angiogenesis in vivo, thereby contributing to accelerated wound healing and tissue recovery after ischemic injury. However, if high levels of CEP and its analogs are accumulated in tissues, it might lead to excessive and pathological vascularization, e.g., in tumors.

EXAMPLE 2

Figure 12:
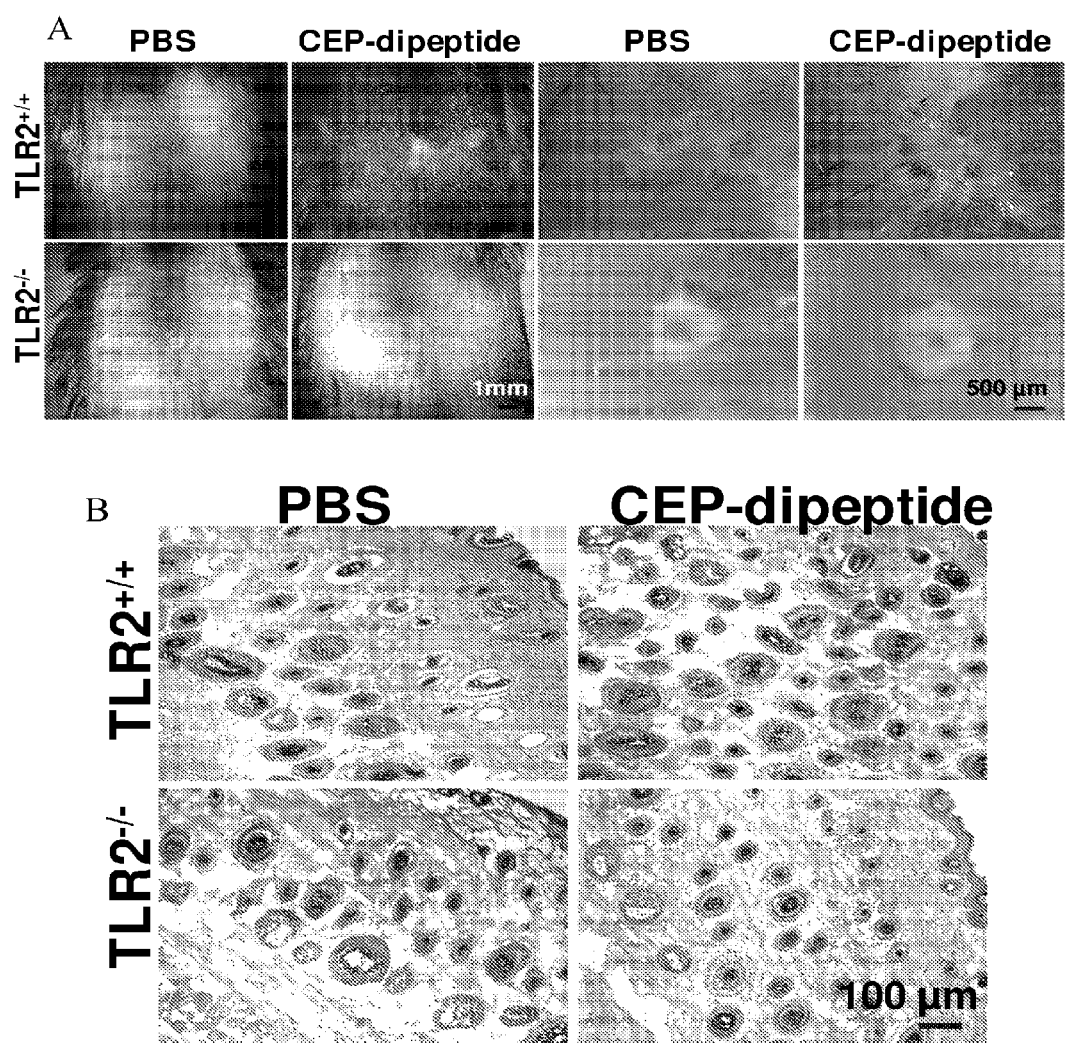
FIG. 12 illustrates (A) images of WT and TLR2 null mice treated with petroleum with or without CEP and (B) images of H&E stained sections of skin showing hair follicles of WT and TLR2 null mice treated with or without CEP.

In this example, as illustrated in FIG. 12-15, we show the effect of CEP dipeptide on hair growth is TLR2 dependent. Petrolatum (1 g) was mixed with CEP-dipeptide (150 microg) for 10 min. Wounds (6 mm in diameter) were created and petrolatum was applied every day (~1 mg of mixture to cover the wound area) for 2 weeks. The reason to apply it every day is that mice roll in their bedding and remove any ointments applied. Higher concentration of 300 microg CEP per 1 g of petroleum was found to have an effect similar to that of 150 microg/g. Concentrations higher than 300 microg CEP per 1 g of petroleum were less effective than 150-300 microg CEP per 1 g. FIG. 12 A shows representative images of WT and TLR2 null mice treated with petroleum with or without CEP. FIG. 12B shows H&E stained sections of skin showing hair follicles of WT and TLR2 null mice treated with or without CEP.

Figure 13:
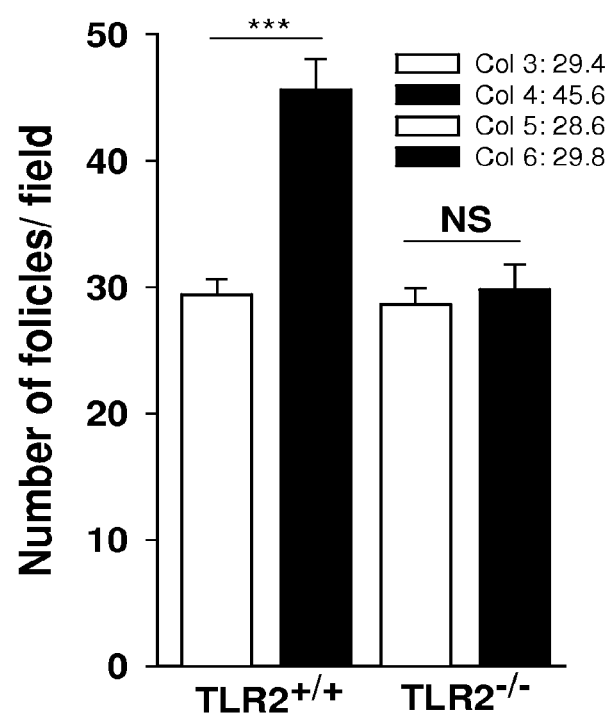
FIG. 13 illustrates a chart showing quantitative results of increased density of hair follicles upon CEP application in TLR2+/+ but not TLR2−/− mice.

FIG. 13 illustrates quantitative results showing increased density of hair follicles upon CEP application in TLR2$^{+/+}$ but not TLR2$^{-/-}$ mice as described above. Please note that hair follicles are known to express TLR2 as a part of immune defense.

Figure 14A:
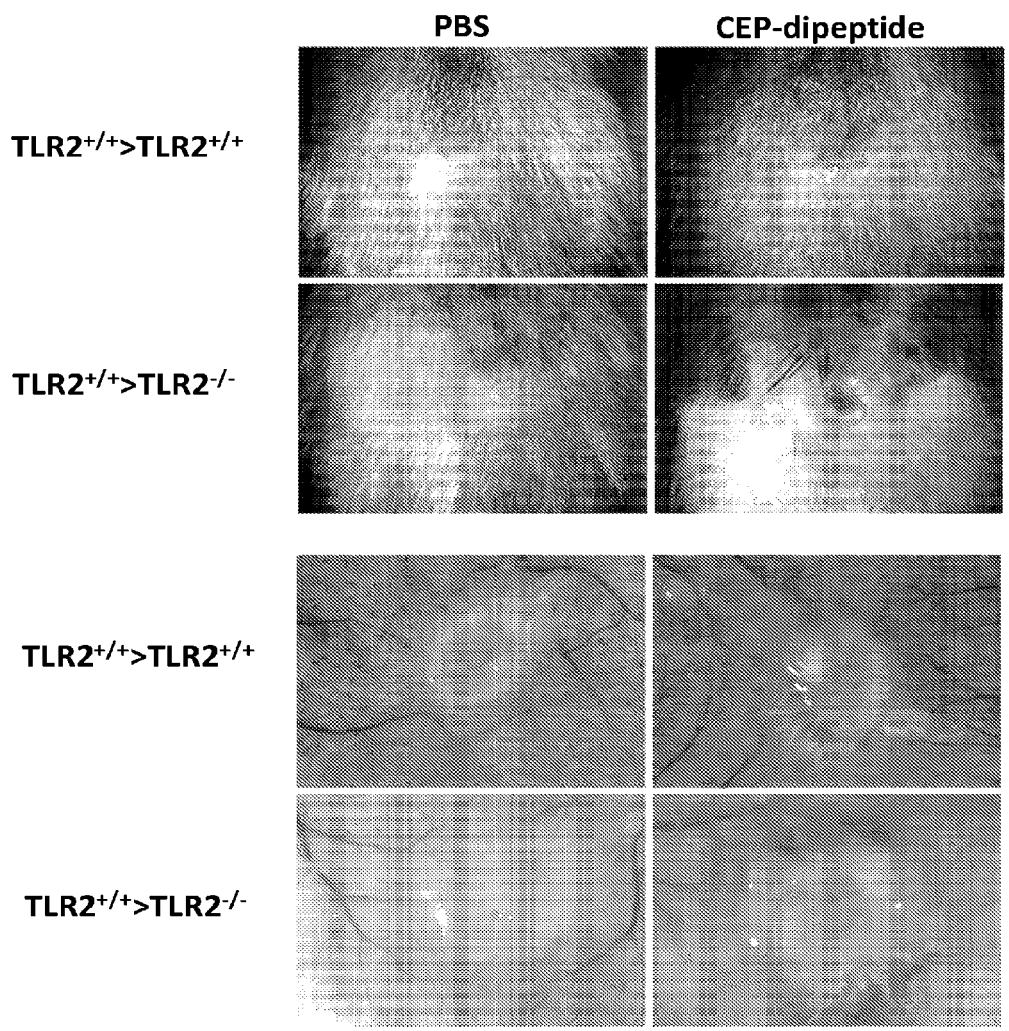
FIG. 14 illustrates (A) images of bone marrow chimeras of WT (TLR2$^{+/+}$) and null (TLR2$^{-/-}$) mice treated with petroleum with or without CEP and (B) images of H&E stained sections of skin showing hair follicles of bone marrow chimeras of WT and TLR2 null mice treated with or without CEP.
Figure 14B:
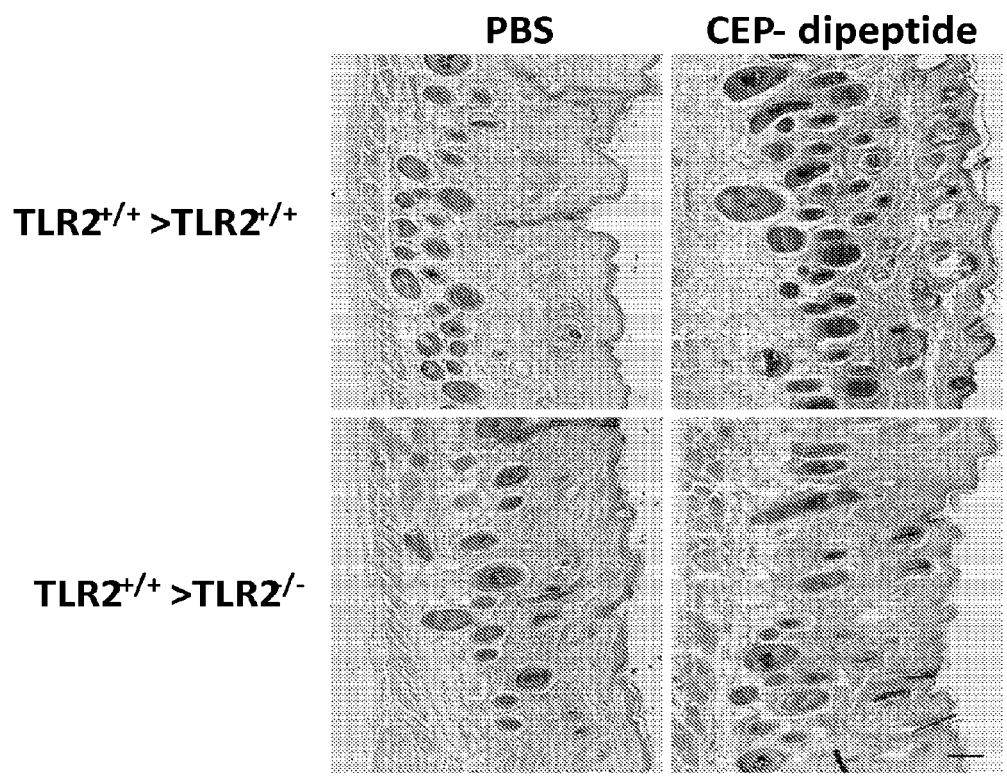
Figure 15:
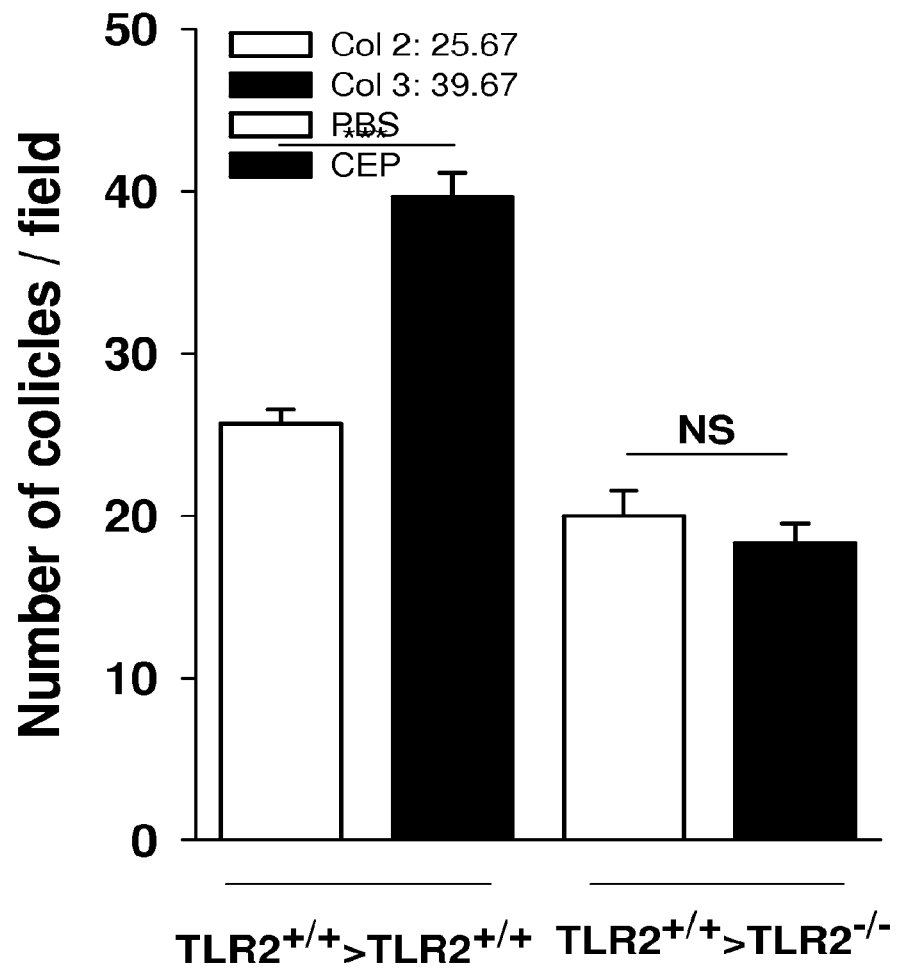
FIG. 15 illustrates a chart showing quantitative results of increased density of hair follicles upon CEP application in bone marrow chimeras of TLR2$^{+/+}$ but not TLR2$^{-/-}$ mice.

FIGS. 14-15 illustrate theame experiment using bone marrow chimeras of TLR2$^{+/+}$ and TLR2$^{-/-}$ mice. The purpose of this experiment is to show that effect of CEP is not bone marrow (inflammation) dependent.

From the above description, those skilled in the art will perceive improvements, changes and modifications. Such improvements, changes, and modifications are within the skill of those in the art and are intended to be covered by the appended claims. All patents, publications, and references recited herein are incorporated by reference in their entirety.

Having described the invention, the following is claimed:

1. A method of promoting hair growth at a skin wound site of a mammalian subject, comprising:
    administering to the skin wound site of the mammalian subject a therapeutically effective amount of a TLR2 agonist that promotes TLR2 activation and hair growth of the mammalian subject, the TLR2 agonist comprising a carboxyethylpyrrole (CEP) adduct or pharmaceutically acceptable salts thereof.

2. The method of claim 1, wherein the therapeutically effective amount is the amount required to increase hair follicle density at the skin wound site of the subject.

3. The method of claim 1, the CEP adduct having the following formula:

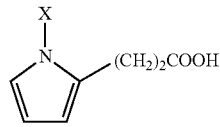

wherein X is a peptide, polypeptide, small molecule, or polymer, and is bound to the amine of the CEP pyrrole or pharmaceutically acceptable salts thereof.

4. The method of claim 3, wherein X is selected from the group consisting of mouse serum albumin and human serum albumin.

5. A method of promoting hair growth at a skin wound site of a mammalian subject, comprising:
    administering to the skin wound site of the mammalian subject a therapeutically effective amount of a TLR2 agonist that promotes TLR2 activation and hair growth at the skin wound site of the mammalian subject, the TLR2 agonist comprising a carboxyethylpyrrole (CEP) adduct having the following formula:

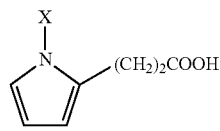

wherein X is selected from the group consisting of a dipeptide, mouse serum albumin and human serum albumin, and is bound to the amine of the CEP pyrrole or pharmaceutically acceptable salts thereof.

6. The method of claim 5, wherein the therapeutically effective amount is the amount required to increase hair follicle density at the skin wound site of the subject.

7. A topical formulation for promoting hair growth at a skin wound site in a mammalian subject, the topical formulation comprising:
    a therapeutically effective amount of a carboxyethylpyrrole (CEP) adduct that promotes TLR2 activation and at least one carrier or pharmaceutically acceptable salts thereof, the topical formulation when administered to the skin wound site of the mammalian subject promoting hair growth at the skin wound site.

8. The topical formulation of claim 7, wherein the therapeutically effective amount is the amount required to increase hair follicle density at the skin wound site of the subject.

9. The topical formulation of claim 7, the CEP adduct having the following formula:

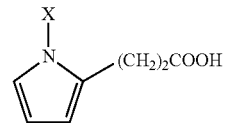

wherein X is a peptide, dipeptide, polypeptide, small molecule, or polymer, and is bound to the amine of the CEP pyrrole and or pharmaceutically acceptable salts thereof.

10. The topical formulation of claim 9, wherein X is selected from the group consisting of mouse serum albumin and human serum albumin.

11. A topical formulation for promoting hair growth at a skin wound site in a mammalian subject, the topical formulation comprising:
    a therapeutically effective amount of a carboxyethylpyrrole (CEP) adduct that promotes TLR2 activation and at least one carrier, the topical formulation when administered to the skin wound site of the subject promoting hair growth at the skin wound site, the CEP adduct having the following formula:

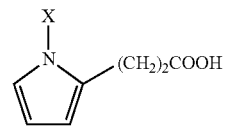

wherein X is selected from the group consisting of a dipeptide, mouse serum albumin and human serum albumin, and is bound to the amine of the CEP pyrrole or pharmaceutically acceptable salts thereof.

12. The topical formulation of claim 11, wherein the therapeutically effective amount is the amount required to increase hair follicle density at the skin wound site of the subject.

* * * * *